(12) United States Patent  (10) Patent No.: US 9,095,416 B2
Meade et al.  (45) Date of Patent: *Aug. 4, 2015

(54) REMOVAL AND REPOSITIONING DEVICES

(71) Applicant: GI Dynamics, Inc., Lexington, MA (US)

(72) Inventors: John C. Meade, Mendon, MA (US); Andy H. Levine, Newton, MA (US); David A. Melanson, Hudson, NH (US); Ronald B. Lamport, Pelham, NH (US); John F. Cvinar, Highland Beach, FL (US)

(73) Assignee: GI Dynamics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/294,786

(22) Filed: Jun. 3, 2014

(65) Prior Publication Data

US 2014/0296768 A1  Oct. 2, 2014

Related U.S. Application Data

(63) Continuation of application No. 13/252,609, filed on Oct. 4, 2011, now Pat. No. 8,771,219, which is a continuation of application No. 12/005,049, filed on Dec. 20, 2007, now Pat. No. 8,057,420, which is a (Continued)

(51) Int. Cl.
*A61F 5/00* (2006.01)
*A61B 17/221* (2006.01)

(Continued)

(52) U.S. Cl.
CPC ............. *A61F 5/0089* (2013.01); *A61B 17/221* (2013.01); *A61F 2/04* (2013.01);

(Continued)

(58) Field of Classification Search
CPC ....... A61F 5/0089; A61F 2/04; A61F 5/0076; A61B 17/221
USPC .................. 604/8–10; 623/1.15, 23.64–23.7; 606/151, 191; 600/37
See application file for complete search history.

(56) References Cited

U.S. PATENT DOCUMENTS 1,899,781 A    2/1933 Twiss
2,464,933 A    3/1949 Kaslow
(Continued)

FOREIGN PATENT DOCUMENTS

DE    33 26 061 A1    2/1984
EP    0423916 B1    4/1991
(Continued)

OTHER PUBLICATIONS

Bethge, N., et al., "Human tissue responses to metal stents implanted in vivo for the palliation of malignant stenoses," Gastrointestinal Endoscopy 43:(1996).

(Continued)

*Primary Examiner* — Philip R Wiest
(74) *Attorney, Agent, or Firm* — Hamilton, Brook, Smith & Reynolds, P.C.

(57) ABSTRACT

A gastrointestinal implant device includes a flexible, floppy sleeve, open at both ends, that extends into the duodenum. The device further includes a collapsible anchor coupled to the proximal portion of the sleeve. The device further includes a drawstring that is threaded through a proximal end of the anchor, and barbs that extend from the exterior surface of the anchor. The collapsible anchor can be a wave anchor. The drawstring can be used to collapse at least a proximal portion of the implant device. This is useful in removing or repositioning the implant device.

15 Claims, 21 Drawing Sheets

Related U.S. Application Data continuation-in-part of application No. 11/318,083, filed on Dec. 22, 2005, now abandoned, said application No. 12/005,049 is a continuation-in-part of application No. 10/858,851, filed on Jun. 1, 2004, now Pat. No. 7,476,256.

(60) Provisional application No. 60/663,352, filed on Mar. 17, 2005, provisional application No. 60/544,527, filed on Feb. 13, 2004, provisional application No. 60/528,084, filed on Dec. 9, 2003.

(51) Int. Cl.
| | | |
|---|---|---|
| *A61F 2/04* | (2013.01) | |
| *A61B 1/00* | (2006.01) | |
| *A61B 1/018* | (2006.01) | |
| *A61B 17/00* | (2006.01) | |
| *A61B 17/22* | (2006.01) | |
| *A61B 17/34* | (2006.01) | |

(52) U.S. Cl.
CPC .......... *A61F 5/0076* (2013.01); *A61B 1/00089* (2013.01); *A61B 1/018* (2013.01); *A61B 2017/00296* (2013.01); *A61B 2017/00336* (2013.01); *A61B 2017/00349* (2013.01); *A61B 2017/2215* (2013.01); *A61B 2017/22035* (2013.01); *A61B 2017/347* (2013.01)

(56) References Cited

U.S. PATENT DOCUMENTS

| | | |
|---|---|---|
| 3,780,740 A | 12/1973 | Rhea |
| 4,133,315 A | 1/1979 | Berman et al. |
| 4,134,405 A | 1/1979 | Smit |
| 4,246,893 A | 1/1981 | Berson |
| 4,265,694 A | 5/1981 | Boretos et al. |
| 4,270,542 A | 6/1981 | Plumley |
| 4,271,827 A | 6/1981 | Angelchik |
| 4,279,251 A | 7/1981 | Rüsch |
| 4,315,509 A | 2/1982 | Smit |
| 4,341,218 A | 7/1982 | U |
| 4,403,604 A | 9/1983 | Wilkinson et al. |
| 4,416,267 A | 11/1983 | Garren et al. |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,763,653 A | 8/1988 | Rockey |
| 4,768,507 A | 9/1988 | Fischell et al. |
| 4,823,808 A | 4/1989 | Clegg et al. |
| 4,846,836 A | 7/1989 | Reich |
| 4,878,905 A | 11/1989 | Blass |
| 4,905,693 A | 3/1990 | Ravo |
| 4,909,789 A | 3/1990 | Taguchi et al. |
| 4,913,141 A | 4/1990 | Hillstead |
| 4,960,106 A | 10/1990 | Kubokawa |
| 4,994,079 A | 2/1991 | Genese et al. |
| 5,035,706 A | 7/1991 | Gianturco et al. |
| 5,037,387 A | 8/1991 | Quinn et al. |
| 5,041,126 A | 8/1991 | Gianturco |
| 5,057,091 A | 10/1991 | Andersen |
| 5,059,166 A | 10/1991 | Fischell et al. |
| 5,104,399 A | 4/1992 | Lazarus |
| 5,123,917 A | 6/1992 | Lee |
| 5,135,516 A | 8/1992 | Sahatjian et al. |
| 5,152,756 A | 10/1992 | Quinn et al. |
| 5,152,782 A | 10/1992 | Kowligi et al. |
| 5,176,617 A | 1/1993 | Fischell et al. |
| 5,190,561 A | 3/1993 | Graber |
| 5,226,429 A | 7/1993 | Kuzmak |
| 5,236,423 A | 8/1993 | Mix et al. |
| 5,246,456 A | 9/1993 | Wilkinson |
| 5,254,133 A | 10/1993 | Seid |
| 5,279,553 A | 1/1994 | Winkler et al. |
| 5,282,824 A | 2/1994 | Gianturco |
| 5,290,294 A | 3/1994 | Cox et al. |
| 5,306,300 A | 4/1994 | Berry |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,322,501 A | 6/1994 | Mahmud-Durrani |
| 5,330,500 A | 7/1994 | Song |
| 5,364,353 A | 11/1994 | Corfitsen et al. |
| 5,387,235 A | 2/1995 | Chuter |
| 5,389,090 A | 2/1995 | Fischell et al. |
| 5,401,241 A | 3/1995 | Delany |
| 5,405,378 A | 4/1995 | Strecker |
| 5,417,697 A | 5/1995 | Wilk et al. |
| 5,423,851 A | 6/1995 | Samuels |
| 5,443,498 A | 8/1995 | Fontaine |
| 5,456,713 A | 10/1995 | Chuter |
| 5,480,423 A | 1/1996 | Ravenscroft et al. |
| 5,492,530 A | 2/1996 | Fischell et al. |
| 5,507,767 A | 4/1996 | Maeda et al. |
| 5,507,771 A | 4/1996 | Gianturco |
| 5,522,880 A | 6/1996 | Barone et al. |
| 5,562,697 A | 10/1996 | Christiansen |
| 5,569,219 A | 10/1996 | Hakki et al. |
| 5,571,173 A | 11/1996 | Parodi |
| 5,605,530 A | 2/1997 | Fischell et al. |
| 5,607,442 A | 3/1997 | Fischell et al. |
| 5,611,787 A | 3/1997 | Demeter et al. |
| 5,624,430 A | 4/1997 | Eton et al. |
| 5,630,797 A | 5/1997 | Diedrich et al. |
| 5,634,928 A | 6/1997 | Fischell et al. |
| 5,639,274 A | 6/1997 | Fischell et al. |
| 5,643,312 A | 7/1997 | Fischell et al. |
| 5,662,713 A | 9/1997 | Andersen et al. |
| 5,665,064 A | 9/1997 | Bodicky et al. |
| 5,669,932 A | 9/1997 | Fischell et al. |
| 5,690,642 A | 11/1997 | Osborne et al. |
| 5,693,084 A | 12/1997 | Chuter |
| 5,695,516 A | 12/1997 | Fischell et al. |
| 5,697,936 A | 12/1997 | Shipko et al. |
| 5,697,971 A | 12/1997 | Fischell et al. |
| 5,713,948 A | 2/1998 | Uflacker |
| 5,715,832 A | 2/1998 | Koblish et al. |
| 5,720,776 A | 2/1998 | Chuter et al. |
| 5,722,984 A | 3/1998 | Fischell et al. |
| 5,730,698 A | 3/1998 | Fischell et al. |
| 5,733,325 A | 3/1998 | Robinson et al. |
| 5,735,859 A | 4/1998 | Fischell et al. |
| 5,735,892 A | 4/1998 | Myers et al. |
| 5,743,874 A | 4/1998 | Fischell et al. |
| 5,749,825 A | 5/1998 | Fischell et al. |
| 5,749,921 A | 5/1998 | Lenker |
| 5,755,777 A | 5/1998 | Chuter |
| 5,759,174 A | 6/1998 | Fischell et al. |
| 5,776,186 A | 7/1998 | Uflacker |
| 5,792,144 A | 8/1998 | Fischell et al. |
| 5,792,172 A | 8/1998 | Fischell et al. |
| 5,800,456 A | 9/1998 | Maeda et al. |
| 5,800,526 A | 9/1998 | Anderson et al. |
| 5,820,584 A | 10/1998 | Crabb |
| 5,830,229 A | 11/1998 | Konya et al. |
| 5,833,707 A | 11/1998 | McIntyre et al. |
| 5,840,009 A | 11/1998 | Fischell et al. |
| 5,843,164 A | 12/1998 | Frantzen et al. |
| 5,855,601 A | 1/1999 | Bessler et al. |
| 5,876,445 A | 3/1999 | Andersen et al. |
| 5,879,282 A | 3/1999 | Fischell et al. |
| 5,879,370 A | 3/1999 | Fischell et al. |
| 5,895,391 A | 4/1999 | Farnholtz |
| 5,897,487 A | 4/1999 | Ouchi |
| 5,910,145 A | 6/1999 | Fischell et al. |
| 5,913,895 A | 6/1999 | Burpee et al. |
| 5,919,225 A | 7/1999 | Lau et al. |
| 5,919,233 A | 7/1999 | Knopf et al. |
| 5,925,063 A | 7/1999 | Khosravi |

(56) References Cited

U.S. PATENT DOCUMENTS

| | | |
|---|---|---|
| 5,962,620 A | 10/1999 | Reich et al. |
| 5,964,771 A | 10/1999 | Beyar et al. |
| 5,976,153 A | 11/1999 | Fischell et al. |
| 6,013,019 A | 1/2000 | Fischell et al. |
| 6,027,508 A | 2/2000 | Ren et al. |
| 6,027,526 A | 2/2000 | Limon et al. |
| 6,035,856 A | 3/2000 | LaFontaine et al. |
| 6,074,673 A | 6/2000 | Guillen |
| 6,086,604 A | 7/2000 | Fischell et al. |
| 6,095,970 A | 8/2000 | Hidaka et al. |
| 6,099,552 A | 8/2000 | Adams |
| 6,102,887 A | 8/2000 | Altman |
| 6,120,533 A | 9/2000 | Fischell |
| 6,120,534 A | 9/2000 | Ruiz |
| 6,132,471 A | 10/2000 | Johlin, Jr. |
| 6,146,323 A | 11/2000 | Fischell |
| 6,152,956 A | 11/2000 | Pierce |
| 6,179,868 B1 | 1/2001 | Burpee et al. |
| 6,187,016 B1 | 2/2001 | Hedges et al. |
| 6,190,403 B1 | 2/2001 | Fischell et al. |
| 6,200,336 B1 | 3/2001 | Pavcnik et al. |
| 6,221,043 B1 | 4/2001 | Fischell et al. |
| 6,221,102 B1 | 4/2001 | Baker et al. |
| 6,241,738 B1 | 6/2001 | Dereume |
| 6,241,757 B1 | 6/2001 | An et al. |
| 6,251,064 B1 | 6/2001 | Silverman et al. |
| 6,251,132 B1 | 6/2001 | Ravenscroft et al. |
| 6,270,521 B1 | 8/2001 | Fischell et al. |
| 6,293,960 B1 | 9/2001 | Ken |
| 6,302,891 B1 | 10/2001 | Nadal |
| 6,302,917 B1 | 10/2001 | Dua et al. |
| 6,315,708 B1 | 11/2001 | Salmon et al. |
| 6,322,538 B1 | 11/2001 | Elbert et al. |
| 6,331,190 B1 | 12/2001 | Shokoohi et al. |
| 6,332,877 B1 | 12/2001 | Michels |
| 6,355,056 B1 | 3/2002 | Pinheiro |
| 6,356,782 B1 | 3/2002 | Sirimanne et al. |
| 6,375,660 B1 | 4/2002 | Fischell et al. |
| 6,383,214 B1 | 5/2002 | Banas et al. |
| 6,387,114 B2 | 5/2002 | Adams |
| 6,401,718 B1 | 6/2002 | Johnson et al. |
| 6,402,779 B1 | 6/2002 | Colone et al. |
| 6,406,792 B1 | 6/2002 | Briquet et al. |
| 6,428,558 B1 | 8/2002 | Jones et al. |
| 6,450,989 B2 | 9/2002 | Dubrul et al. |
| 6,458,074 B1 | 10/2002 | Matsui et al. |
| 6,485,409 B1 | 11/2002 | Voloshin et al. |
| 6,485,515 B2 | 11/2002 | Strecker |
| 6,508,833 B2 | 1/2003 | Pavcnik et al. |
| 6,520,985 B1 | 2/2003 | Burpee et al. |
| 6,524,335 B1 | 2/2003 | Hartley et al. |
| 6,524,336 B1 | 2/2003 | Papazolgou et al. |
| 6,530,951 B1 | 3/2003 | Bates et al. |
| 6,537,247 B2 | 3/2003 | Shannon |
| 6,540,775 B1 | 4/2003 | Fischell et al. |
| 6,540,789 B1 | 4/2003 | Silverman et al. |
| 6,544,291 B2 | 4/2003 | Taylor |
| 6,547,817 B1 | 4/2003 | Fischell et al. |
| 6,558,400 B2 | 5/2003 | Deem et al. |
| 6,558,429 B2 | 5/2003 | Taylor |
| 6,565,597 B1 | 5/2003 | Fearnot et al. |
| 6,569,181 B1 | 5/2003 | Burns |
| 6,589,213 B2 | 7/2003 | Reydel |
| 6,589,275 B1 | 7/2003 | Ivancev et al. |
| 6,623,518 B2 | 9/2003 | Thompson et al. |
| 6,635,069 B1 | 10/2003 | Teoh et al. |
| 6,635,079 B2 | 10/2003 | Unsworth et al. |
| 6,645,239 B1 | 11/2003 | Park et al. |
| 6,652,555 B1 | 11/2003 | VanTassel et al. |
| 6,656,194 B1 | 12/2003 | Gannoe et al. |
| 6,669,722 B2 | 12/2003 | Chen et al. |
| 6,675,809 B2 | 1/2004 | Stack et al. |
| 6,676,692 B2 | 1/2004 | Rabkin et al. |
| 6,695,875 B2 | 2/2004 | Stelter et al. |
| 6,699,263 B2 | 3/2004 | Cope |
| 6,699,278 B2 | 3/2004 | Fischell et al. |
| 6,706,061 B1 | 3/2004 | Fischell et al. |
| 6,716,240 B2 | 4/2004 | Fischell et al. |
| 6,736,840 B2 | 5/2004 | Fischell et al. |
| 6,740,121 B2 | 5/2004 | Geitz |
| 6,755,869 B2 | 6/2004 | Geitz |
| 6,764,518 B2 | 7/2004 | Godin |
| 6,773,440 B2 | 8/2004 | Gannoe et al. |
| 6,776,791 B1 | 8/2004 | Stallings et al. |
| 6,802,868 B2 | 10/2004 | Silverman et al. |
| 6,821,291 B2 | 11/2004 | Bolea et al. |
| 6,845,776 B2 | 1/2005 | Stack et al. |
| 6,860,901 B1 | 3/2005 | Baker et al. |
| 6,936,065 B2 | 8/2005 | Khan et al. |
| 6,960,233 B1 | 11/2005 | Berg et al. |
| 7,011,673 B2 | 3/2006 | Fischell et al. |
| 7,025,791 B2 | 4/2006 | Levine et al. |
| 7,033,384 B2 | 4/2006 | Gannoe et al. |
| 7,037,327 B2 | 5/2006 | Salmon et al. |
| 7,037,344 B2 | 5/2006 | Kagan et al. |
| 7,054,690 B2 | 5/2006 | Imran |
| 7,081,132 B2 | 7/2006 | Cook et al. |
| 7,087,088 B2 | 8/2006 | Berg et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,175,660 B2 | 2/2007 | Cartledge et al. |
| 7,211,114 B2 | 5/2007 | Bessler et |
| 7,220,237 B2 | 5/2007 | Gannoe et al. |
| 7,220,284 B2 | 5/2007 | Kagan et al. |
| 7,267,694 B2 | 9/2007 | Levine et al. |
| 7,314,489 B2 | 1/2008 | McKenna et al. |
| 7,329,285 B2 | 2/2008 | Levine et al. |
| 7,338,520 B2 | 3/2008 | Bailey et al. |
| 7,347,875 B2 | 3/2008 | Levine et al. |
| 7,354,454 B2 | 4/2008 | Stack et al. |
| 7,476,256 B2 | 1/2009 | Meade et al. |
| 8,057,420 B2 * | 11/2011 | Meade et al. ............. 604/8 |
| 8,771,219 B2 * | 7/2014 | Meade et al. ............. 604/8 |
| 2001/0020190 A1 | 9/2001 | Taylor |
| 2002/0022853 A1 | 2/2002 | Swanson et al. |
| 2002/0032487 A1 | 3/2002 | Dua et al. |
| 2002/0065545 A1 | 5/2002 | Leonhardt et al. |
| 2002/0082639 A1 | 6/2002 | Broome et al. |
| 2002/0091439 A1 | 7/2002 | Baker et al. |
| 2002/0120277 A1 | 8/2002 | Hauschild et al. |
| 2002/0143387 A1 * | 10/2002 | Soetikno et al. ............. 623/1.15 |
| 2002/0147489 A1 | 10/2002 | Hong et al. |
| 2002/0151953 A1 | 10/2002 | Chobotov et al. |
| 2002/0177890 A1 | 11/2002 | Lenker |
| 2002/0183768 A1 | 12/2002 | Deem et al. |
| 2002/0183786 A1 | 12/2002 | Girton |
| 2002/0188344 A1 | 12/2002 | Bolea et al. |
| 2002/0193828 A1 | 12/2002 | Griffin et al. |
| 2003/0032941 A1 | 2/2003 | Boyle et al. |
| 2003/0040804 A1 | 2/2003 | Stack et al. |
| 2003/0040808 A1 | 2/2003 | Stack et al. |
| 2003/0050684 A1 | 3/2003 | Abrams et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0149467 A1 | 8/2003 | Linder et al. |
| 2003/0153927 A1 | 8/2003 | DiPoto et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208260 A1 | 11/2003 | Lau et al. |
| 2003/0216749 A1 | 11/2003 | Ishikawa et al. |
| 2003/0233140 A1 | 12/2003 | Hartley et al. |
| 2004/0019388 A1 | 1/2004 | Starkebaum |
| 2004/0024386 A1 | 2/2004 | Deem et al. |
| 2004/0037865 A1 | 2/2004 | Miller |
| 2004/0039452 A1 | 2/2004 | Bessler |
| 2004/0044357 A1 | 3/2004 | Gannoe et al. |
| 2004/0082963 A1 | 4/2004 | Gannoe et al. |

(56) References Cited

U.S. PATENT DOCUMENTS

| | | |
|---|---|---|
| 2004/0092892 A1 | 5/2004 | Kagan et al. |
| 2004/0092974 A1 | 5/2004 | Gannoe et al. |
| 2004/0093065 A1 | 5/2004 | Yachia et al. |
| 2004/0098079 A1 | 5/2004 | Hartley et al. |
| 2004/0107004 A1 | 6/2004 | Levine et al. |
| 2004/0117004 A1 | 6/2004 | Osborne et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122470 A1 | 6/2004 | Deem et al. |
| 2004/0133147 A1 | 7/2004 | Woo |
| 2004/0136971 A1 | 7/2004 | Scharp et al. |
| 2004/0138525 A1 | 7/2004 | Saadat et al. |
| 2004/0138529 A1 | 7/2004 | Wiltshire et al. |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158229 A1 | 8/2004 | Quinn |
| 2004/0158331 A1 | 8/2004 | Stack et al. |
| 2004/0172042 A1 | 9/2004 | Suon et al. |
| 2004/0172063 A1 | 9/2004 | Li et al. |
| 2004/0172088 A1 | 9/2004 | Knudson et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0181242 A1 | 9/2004 | Stack et al. |
| 2004/0193093 A1 | 9/2004 | Desmond, III |
| 2004/0193261 A1 | 9/2004 | Berreklouw |
| 2004/0210243 A1 | 10/2004 | Gannoe et al. |
| 2004/0215212 A1 | 10/2004 | Teague |
| 2004/0220682 A1 | 11/2004 | Levine et al. |
| 2004/0236401 A1 | 11/2004 | Shin et al. |
| 2004/0249362 A1 | 12/2004 | Levine et al. |
| 2005/0004681 A1 | 1/2005 | Stack et al. |
| 2005/0043601 A1 | 2/2005 | Kilcoyne et al. |
| 2005/0043817 A1 | 2/2005 | McKenna et al. |
| 2005/0049612 A1 | 3/2005 | Urbanski et al. |
| 2005/0049718 A1 | 3/2005 | Dann et al. |
| 2005/0055039 A1 | 3/2005 | Burnett et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0085787 A1 | 4/2005 | Laufer |
| 2005/0085923 A1 | 4/2005 | Levine et al. |
| 2005/0090873 A1 | 4/2005 | Imran |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149114 A1 | 7/2005 | Cartledge et al. |
| 2005/0171556 A1 | 8/2005 | Murphy |
| 2005/0192614 A1 | 9/2005 | Binmoeller |
| 2005/0216040 A1 | 9/2005 | Gertner et al. |
| 2005/0216042 A1 | 9/2005 | Gertner |
| 2005/0221072 A1 | 10/2005 | Dubrow et al. |
| 2005/0228415 A1 | 10/2005 | Gertner |
| 2005/0228504 A1 | 10/2005 | Demarais |
| 2005/0240279 A1 | 10/2005 | Kagan et al. |
| 2005/0256587 A1 | 11/2005 | Egan |
| 2005/0267499 A1 | 12/2005 | Stack et al. |
| 2005/0267533 A1 | 12/2005 | Gertner |
| 2006/0009858 A1 | 1/2006 | Levine et al. |
| 2006/0064120 A1 | 3/2006 | Levine et al. |
| 2006/0106332 A1 | 5/2006 | Knudson et al. |
| 2006/0155312 A1 | 7/2006 | Levine et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0212042 A1 | 9/2006 | Lamport et al. |
| 2006/0265082 A1 | 11/2006 | Meade et al. |
| 2006/0271175 A1 | 11/2006 | Woolfson et al. |
| 2006/0287734 A1 | 12/2006 | Stack et al. |
| 2007/0005147 A1 | 1/2007 | Levine et al. |
| 2007/0010864 A1 | 1/2007 | Dann et al. |
| 2007/0027548 A1 | 2/2007 | Levine et al. |
| 2007/0032879 A1 | 2/2007 | Levine et al. |
| 2007/0049801 A1 | 3/2007 | Lamport et al. |
| 2007/0083271 A1 | 4/2007 | Levine et al. |
| 2008/0071383 A1 | 3/2008 | Levine et al. |
| 2008/0097466 A1 | 4/2008 | Levine et al. |
| 2008/0103604 A1 | 5/2008 | Levine et al. |
| 2008/0208357 A1 | 8/2008 | Melanson et al. |
| 2008/0223476 A1 | 9/2008 | Stinson |
| 2008/0234834 A1 | 9/2008 | Meade et al. |
| 2012/0029413 A1 | 2/2012 | Meade et al. |

FOREIGN PATENT DOCUMENTS

| | | |
|---|---|---|
| EP | 0 480 667 B1 | 4/1992 |
| EP | 0278937 B1 | 10/1993 |
| EP | 0 506 918 B1 | 1/1996 |
| EP | 0754017 B1 | 1/1997 |
| EP | 0843538 B1 | 5/1998 |
| EP | 0 857 471 A2 | 8/1998 |
| EP | 0935977 A2 | 8/1999 |
| EP | 0935977 A3 | 8/1999 |
| EP | 1481649 A1 | 12/2004 |
| EP | 1504778 A2 | 3/2005 |
| EP | 1504778 A3 | 3/2005 |
| JP | 04212348 | 8/1992 |
| WO | WO 92/06734 A1 | 4/1992 |
| WO | WO 95/05132 | 2/1995 |
| WO | WO 97/03624 A1 | 2/1997 |
| WO | WO 98/22045 A | 5/1998 |
| WO | WO 99/23953 | 5/1999 |
| WO | WO 99/44536 A | 9/1999 |
| WO | WO 00/12027 A1 | 3/2000 |
| WO | WO 00/28922 A1 | 5/2000 |
| WO | WO 00/32137 | 6/2000 |
| WO | WO 00/42945 A1 | 7/2000 |
| WO | WO 00/42949 A2 | 7/2000 |
| WO | WO 01/12256 A1 | 2/2001 |
| WO | WO 01/35861 A1 | 5/2001 |
| WO | WO 01/45485 A2 | 6/2001 |
| WO | WO 02/081019 A1 | 10/2002 |
| WO | WO 02/096327 A2 | 12/2002 |
| WO | WO 03/017882 A2 | 3/2003 |
| WO | WO 03/073961 | 9/2003 |
| WO | WO 03/086246 A1 | 10/2003 |
| WO | WO 03/086247 A1 | 10/2003 |
| WO | WO 03/086360 A1 | 10/2003 |
| WO | WO 03/094785 A1 | 11/2003 |
| WO | WO 04/000169 A1 | 12/2003 |
| WO | WO 2004/004542 A2 | 1/2004 |
| WO | WO 2004/004542 A3 | 1/2004 |
| WO | WO 2004/014237 A1 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064680 A1 | 8/2004 |
| WO | WO 2004/064682 A1 | 8/2004 |
| WO | WO 2004/064685 A1 | 8/2004 |
| WO | WO 2004/069331 A2 | 8/2004 |
| WO | WO 2004/069332 A1 | 8/2004 |
| WO | WO 2004/073782 A1 | 9/2004 |
| WO | WO 2004/087014 A2 | 10/2004 |
| WO | WO 2004/087233 A2 | 10/2004 |
| WO | WO 2004/093639 A2 | 11/2004 |
| WO | WO 2004/093639 A3 | 11/2004 |
| WO | WO 2005/011533 A1 | 2/2005 |
| WO | WO 2005/060869 A1 | 7/2005 |
| WO | WO 2005/060882 A1 | 7/2005 |
| WO | WO 2005/082296 A1 | 9/2005 |
| WO | WO 2005/110280 A2 | 11/2005 |
| WO | WO 2005/110280 A3 | 11/2005 |
| WO | WO 2005/117716 A2 | 12/2005 |
| WO | WO 2005/118049 A1 | 12/2005 |
| WO | WO 2005/120363 A1 | 12/2005 |

(56) References Cited

FOREIGN PATENT DOCUMENTS

| WO | WO 2006/016894 A1 | 2/2006 |
|---|---|---|
| WO | WO 2006/034062 A1 | 3/2006 |
| WO | WO 2006/078781 A1 | 7/2006 |
| WO | WO 2006/078927 A1 | 7/2006 |
| WO | WO 2006/088578 A1 | 8/2006 |
| WO | WO 2006/102012 A1 | 9/2006 |
| WO | WO 2006/133311 A2 | 12/2006 |

OTHER PUBLICATIONS

Binkert, C. A., et al., "Benign and Malignant Stenoses of the Stomach and Duodenum: Treatment with Self-expanding Metallic Endoprostheses," Radiology 199:335-338 (1996).
CHOOSTENT™, Covered Esophageal Stent, Instructions, Retrieved from the Internet (http://mitech.co.kr/uploads/images/282/use guide esophachoo_english.pdf) on Jul. 26, 2005.
Cwikiel, W., et al., "Self-expanding Stent in the Treatment of Benign Esophageal Strictures: Experimental Study in Pigs and Presentation of Clinical Cases," Radiology 187: 667-671 (1993).
Dolan, K. et al., "Treating Diabetes in the Morbidly Obese by Laproscopic Gastric Banding," Obesity Surgery 13:439-443 (2003).
Dormann, A.J., et al., "Self-expanding Metallic Stents for Continous Dilatation of Benign Stenosis in Gastrointestinal Tract—First Results of Long-term Follow-up in Interim Stent Application in Pyloric and Colonic Obstructions," Z. Gastroenterol. 39:957/960 (2001).
Feretis, C., et al., "Palliation of Malignant Gastric Outlet Obstruction with Self-Expanding Metal Stents," Endoscopy 28:225-228 (1996).
Gray, Henry, "The Vascular System," In *Anatomy, Descriptive and Surgical, 15th Edition*, (Bounty Books:NY), T.P. Pick and R. Howden, eds., pp. 1126-1128 (1977).
Hwang, J.C., et al., "Covered Retrievable Tracheobronichial Hinged Stent: An Experimental Study in Dogs," J. Vase. Interv. Radiol., 12:1429-1436 (2001).
Irie, T., et al., "Relocatable Gianturco Expandable Metallic Stents," Radiology 178:575,578 (1991).
Lee, B.H., et al., "New Self-Expandable Spiral Metallic Stent: Preliminary clinical Evaluation in Malignant Biliary Obstruction," J. Vase Intery Radiol., 6(4):635,340 (1995).
Lee, S.H., "The Role of Oesophageal Stenting in the Non-Surgical Management of Oesophageal Strictures," The British J. of Radiology 74:891,900 (2001).
Park, K.B., et al., "Malignant Obstruction of Gastric Outlet and Duodenum: Palliation with Flexible Covered Metallic Stents," Radiology 219:679-683 (2001).
Parodi, J.C., M.D., "Endovascular Repair of Abdominal Aortic Aneurysms," *Advances in Vascular Surgery*, vol. 1, pp. 85-105 (1993).
Pories, W.J., "Why Does the Gastric Bypass Control Type 2 Diabetes Mellitus?" Obesity Surgery, 2:303-313 (1992).
Pories, W.J., et al., "Etiology of Type II Diabetes Mellitus: Role of the Foregut," World J. Surg., 25:527-531 (2001).
Rubino, F. and J. Marescaux, "Effect of Duodenal-Jejunal Exclusion in a Non-obese Animal Model of Type 2 Diabetes, A New Perspective for an Old Disease," Annals of Surgery 239(1):(2004).
Rubino, F., et al., "Potential of Surgery for Curing Type 2 Diabetes Mellitus," Annals of Surgery, 236(5):554-559 (2002).
Sandha, G. S. and Marcon, N. E., "Expandable Metal Stents for Benign Esophageal Obstruction," Gastrointestinal Endoscopy Clinics of North America 9:437-446 (1999).
Shim, C.S., et al., "Fixation of a Modified Covered Esophageal Stent: Its Clinical Usefulness for Preventing Stent Migration," Endoscopy 33(10):843-848 (2001).
Song, H.Y., et al., "Benign and Malignant Esophageal Strictures: Treatment with a Polyurethane-Covered Retrievable Expandable Metallic Stent," Radiology 203:747,752 (1997).
Song, H.Y., et al., "Covered Retrievable Expandable Nitinol Stents in Patients with Benign Esophageal Strictures: Initial Experience," Radiology 217:551/557 (2000).
Song, H.Y., et al., "Tracheobronchial Strictures: Treatment with a Polyurethane-Covered Retrievable Expandable Nitinol Stent/Initial Experience," Radiology 213:905,912 (1999).
Yates III, M. R., et al., "Palliation of Malignant Gastric and Small Intestinal Strictures With Self-Expandable Metal Stents," Endoscopy 30:266-272 (1998).
Yoon, C.J., et al., "Removal of Retrievable Esophageal and Gastrointestinal Stents: Experience in 113 Patients," American J. of Roentgenology 183:1437,1444 (2004).
International Search Report, International Application No. PCT/US2008/013540, mailed on Mar. 26, 2009, "Porous Barbs for Long-term Anchoring in the Gastrointestinal Tract".
Written Opinion of the International Searching Authority, International Application No. PCT/US2008/013540, mailed on Mar. 26, 2009 "Porous Barbs for Long-term Anchoring in the Gastrointestinal Tract".
Non-Final Office Action dated Oct. 2, 2009 for U.S. Appl. No. 11/318,083, "Removal and Repositioning Devices".
Final Office Action dated Oct. 26, 2010 for U.S. Appl. No. 11/318,083, "Removal and Repositioning Devices".
Non-Final Office Action dated Jun. 23, 2010 for U.S. Appl. No. 11/318,083, "Removal and Repositioning Devices".
Final Office Action dated Mar. 17, 2009 for U.S. Appl. No. 11/318,083, "Removal and Repositioning Devices".
Non-Final Office Action dated Sep. 12, 2008 for U.S. Appl. No. 11/318,083, "Removal and Repositioning Devices".
Non-Final Office Action dated Nov. 25, 2013 for U.S. Appl. No. 13/252,609, "Gastrointestinal Implant With Drawstring".
Final Office Action dated Dec. 16, 2010 for U.S. Appl. No. 12/005,049, "Gastrointestinal Implant With Drawstring".
Non-Final Office Action dated May 26, 2010 for U.S. Appl. No. 12/005,049, "Gastrointestinal Implant With Drawstring".

* cited by examiner

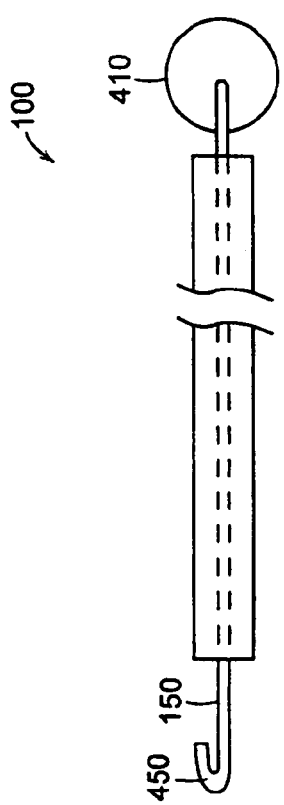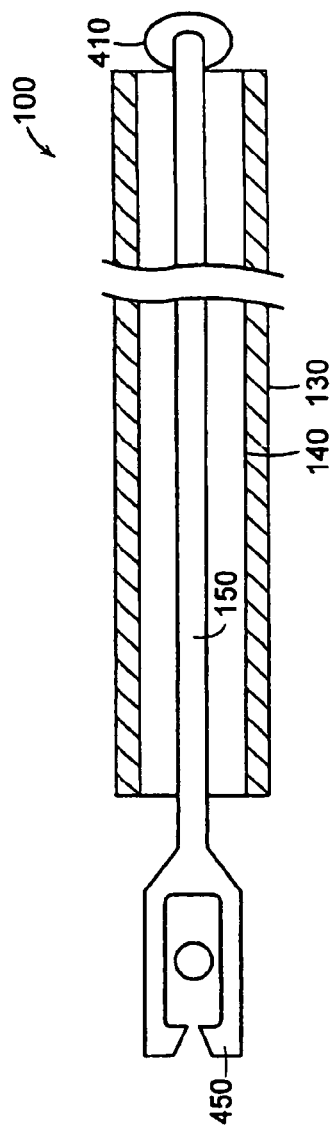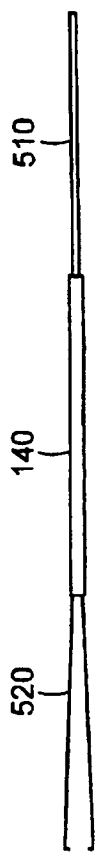

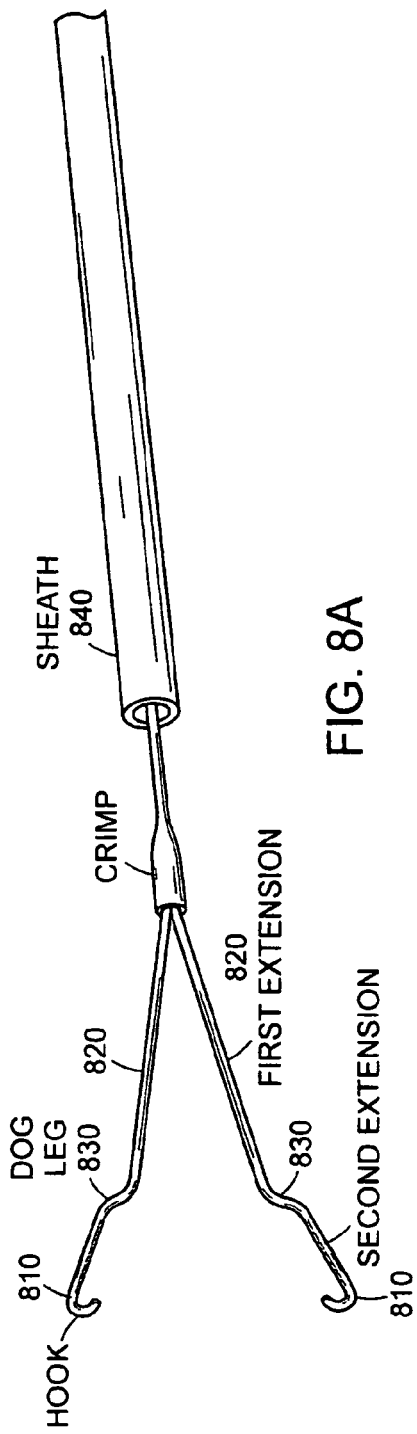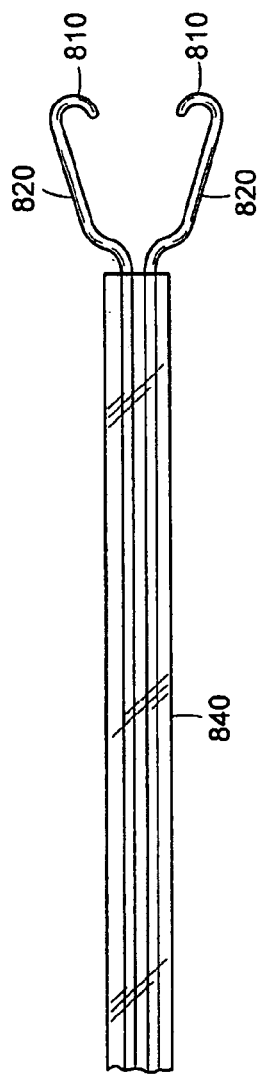
FIG. 8A
FIG. 8B

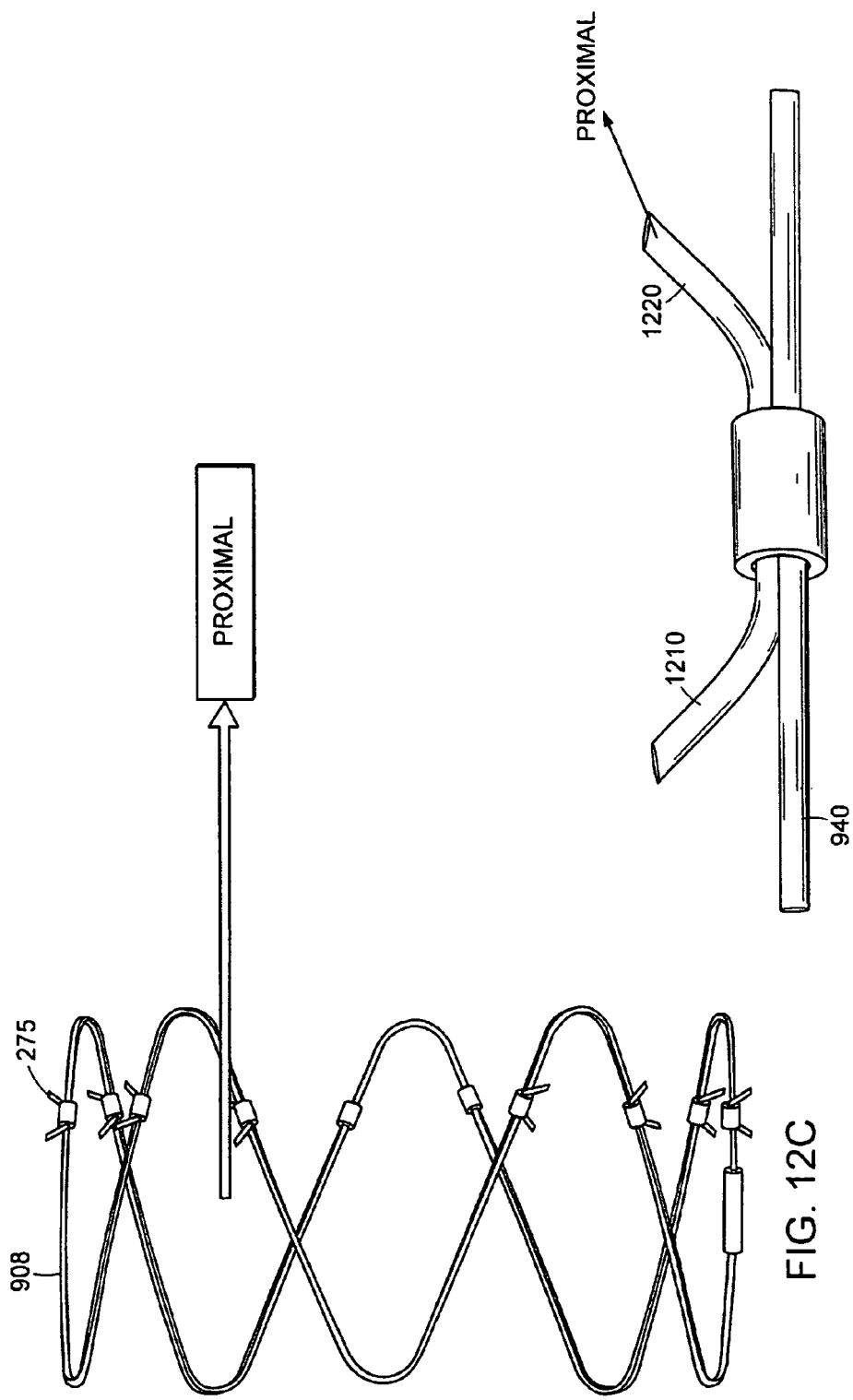

REMOVAL AND REPOSITIONING DEVICES

RELATED APPLICATIONS

This application is a continuation of U.S. application Ser. No. 13/252,609, filed Oct. 4, 2011 which is a continuation of U.S. application Ser. No. 12/005,049, filed Dec. 20, 2007, now U.S. Pat. No. 8,057,420, which is a continuation-in-part of U.S. application Ser. No. 11/318,083, filed Dec. 22, 2005, which claims the benefit of U.S. Provisional Application No. 60/663,352, filed Mar. 17, 2005; and Ser. No. 12/005,049 also is a continuation-in-part of U.S. application Ser. No. 10/858,851, filed Jun. 1, 2004, now U.S. Pat. No. 7,476,256, which claims the benefit of U.S. Provisional Application Nos. 60/544,527, filed Feb. 13, 2004 and 60/528,084, filed Dec. 9, 2003. The entire teachings of the above applications are incorporated herein by reference.

BACKGROUND OF THE INVENTION

Gastrointestinal sleeves can be used to treat obesity or diabetes. To keep the sleeve in place, an anchoring device is needed. Anchoring can include stents or conventional surgical techniques, such as sutures, staples, surgical adhesives, and others. At least some anchoring devices use an interference fit, placing an implant device having a relaxed diameter larger than the diameter offered by the intestine. Other anchoring devices may include barbs that are adapted to penetrate into the surrounding muscular tissue of the gastrointestinal tract.

Often, these gastrointestinal sleeves, due to the complex structure of the anchoring device, may not be removed without damaging surrounding tissue, unless by resection.

SUMMARY OF THE INVENTION

The present invention relates to gastrointestinal devices, methods, and apparatus for removing and/or repositioning the gastrointestinal devices from a natural bodily lumen. In certain embodiments, a gastrointestinal implant includes a flexible, floppy sleeve. The sleeve is open at both ends and extends into the duodenum, preferably at least one foot. The implant also includes a collapsible anchor that is coupled to the proximal portion of the sleeve. The implant can further include a drawstring that is threaded through a proximal end of the anchor. Finally, the implant can include rigid barbs at a fixed angle extending from the exterior surface of the anchor.

In certain embodiments, the anchor includes interconnected struts. The sleeve can have a webbing material at the proximal portion of the sleeve, where the webbing material is coupled to the struts. The drawstring can be woven through holes in the webbing material.

In certain embodiments, the drawstring can be woven over and under the struts through a single hole between the struts. The implant can also include a second drawstring. The second drawstring can be woven through a single hole over and under the struts. Alternatively, the second drawstring can also be woven through pairs of holes in the webbing material. In one embodiment, the anchor is a wave anchor.

A method for repositioning (including removal of) a gastrointestinal implant is also described. The method includes first engaging a drawstring that is disposed on the implantable device. At least a proximal portion of the device is collapsed by pulling on the drawstring. Finally, the device is moved within the natural bodily lumen. The device can also be removed from the patient's body if desired.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 4A-4B show an alternative embodiment of the invention using a rotary actuator;

FIG. 5 shows an alternative embodiment using a rat-tooth grasper;

FIGS. 8A-8B show an alternative embodiment of a grasper;

FIGS. 12A-12D show an embodiment of barbs on a gastrointestinal implant device.

DETAILED DESCRIPTION OF THE INVENTION

A description of preferred embodiments of the invention follows.

Gastrointestinal implants can be used for a number of treatments, at least some of which are described in U.S. patent application Ser. No. 7,025,791 B2, filed on Jan. 9, 2003, that claimed the benefit of U.S. Provisional Application 60/430,320 filed on Dec. 2, 2002, and incorporated herein by reference in its entirety. Implants placed within the gastrointestinal tract are typically subject to substantial mechanical forces related to the digestion process. For example, an implant placed within the intestine, distal to the pyloric sphincter, will be subjected to peristaltic forces tending to push and pull the implant along the intestine. To keep the implant in place, an anchoring device is required. Anchoring can include conventional surgical techniques, such as sutures, staples, surgical adhesives, etc. Anchoring within the intestine, however, poses a unique set of challenges. At least some anchoring devices use an interference fit, placing an implant device having a relaxed diameter larger than the diameter offered by the intestine. Other anchoring devices use barbs that are adapted to penetrate into the surrounding muscular tissue of the gastrointestinal tract. Examples of anchors used for anchoring implants are described in U.S. patent application Ser. No. 10/858,852 filed on Jun. 1, 2004, claiming the benefit of U.S. Provisional Application No. 60/528,084 filed on Dec.

9, 2003, and U.S. Provisional Application No. 60/544,527, filed on Feb. 13, 2004, all incorporated herein in their entireties by reference.

Anchors relying on interference fit, barbs, or a combination of both typically have relaxed dimensions greater than the normal open diameter of the intestine (e.g., greater than twenty five millimeters in an adult human). For example, the implant may be delivered to the intended location in a compressed state using a catheter having an internal diameter of only about 12 millimeters. When the implant is deployed within the intestine it expands to its implanted size. For example, to place an implant into the proximal duodenum, a catheter can be inserted through the patient's nose or mouth, through the esophagus, stomach and pyloric sphincter. The implanted devices can be compressed again prior to and/or during repositioning or removal.

Figure 1:
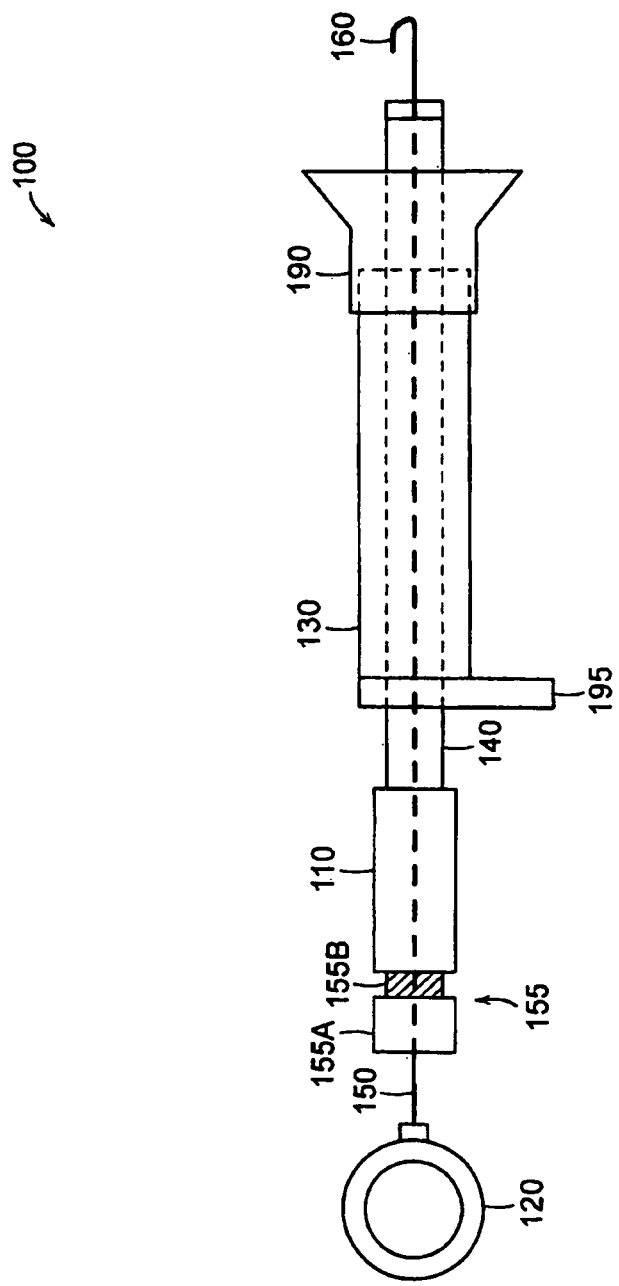
FIG. 1 shows an exemplary embodiment of a repositioning device.

One embodiment of removing or repositioning a gastrointestinal implant device is shown in FIG. 1. The repositioning device 100 may include a handle 110 supporting an actuator 120. The repositioning device 100 further may include an elongated member 150, such as a wire. The elongated member 150 is slidably disposed within the handle 110. The actuator 120 is adapted to attach to a proximal end of the elongated member 150. The repositioning device 100 further may include an inner tube 140. The inner tube 140 defines a lumen within which the elongated member 150 is slidably disposed. The inner tube 140 is adapted for insertion into a natural bodily lumen through an endoscope working channel or a catheter. The inner tube 140 is fixed to a distal end of the handle 110.

A grasper 160, a hook in this embodiment, is coupled at a distal end of the elongated member 150 and is adapted to grasp a feature of an implantable device. For example, a drawstring as described in FIG. 11, is provided on some implantable devices such that manipulation of the drawstring can reduce at least one dimension (e.g., the diameter) of the implantable device.

The elongated member 150 slidably fits through a hole within the handle 110, and is attached to the actuator 120. The actuator 120 and the handle 110 may be operated manually from a site external to a body. For example, the handle 110 and the actuator 120 can be used to maneuver the elongated member 150 and grasper 160 disposed at the distal end of the elongated member 150. The handle 110 may also be manually manipulated to maneuver the inner tube 140.

The elongated member 150 may be several feet in length. Preferably, the elongated member 150 is formed of a flexible material to facilitate navigation through a medical instrument, for example, through the working channel of an endoscope within a natural bodily lumen. Further, the elongated member 150 should be composed of a biocompatible material. Such materials may include polymers and certain metals, such as Nitinol or stainless steel. The elongated member 150 is coupled at its distal end to the grasper 160.

In some embodiments, the grasper 160 may be a hook. The grasper 160 is attached to the distal end of the elongated member 150. The grasper 160 may be any means of grasping a drawstring of an implantable device. The grasper 160 may be attached to the elongated member 150 by various mechanical, chemical, welding or bonding means. The grasper 160 may be formed of a biocompatible material such as polymers and metals such as Nitinol or stainless steel. In one embodiment, the distal end of the elongated member 150 is shaped to form a hook.

The grasper 160 attached to a distal portion of the elongated member 150, is disposed within a lumen of the inner tube 140. The inner tube 140 may be several feet in length in order to extend from a proximal portion of an implantable device to outside of a body. The dimensions of the inner tube may be such that it adapts to the working channel of an endoscope. The inner tube 140 may be made of a biocompatible and flexible material such as certain polymers. Such polymers may include silicone, polyurethane, polyethylene and certain low friction fluoropolymer materials such as PTFE, PFA or FEP. In one embodiment, the grasper 160 is coupled to a grasper locking mechanism 155 through the elongated member 150. The grasper locking mechanism 155 is disposed at a proximal portion of the elongated member 150. The grasper locking mechanism 155 locks in place the elongated member 150 coupled to the grasper 160, when the grasper 160 has pulled the drawstring of the implantable device, and the implantable device has thus been radially collapsed. In one embodiment, the grasper locking mechanism 155 is a compression-type locking mechanism. The grasper locking mechanism 155 includes a member 155A, which is threaded onto member 155B. Member 155B is adapted to be fixed within a proximal opening of the handle 110. The elongated member 160 is slidably disposed through the grasper locking mechanism 155, when the grasper locking mechanism 155 is left unlocked. When the grasper 160 has grasped the collapsed implantable device, the grasper locking mechanism 155 may be locked, thus tightening around the elongated member 150 so that the elongated member 160 is fixed and is no longer slideable within the inner tube 140. In other embodiments, the grasper 160 coupled to the elongated member 150 may be locked using other locking mechanisms such as other types of compression locks, screw-type locks, pincher type locks, clamp type locks or any means capable of locking the grasper 160 coupled to the elongated member 150 in place. Example locking devices and methods of using locking devices are described in U.S. patent application Ser. No. 11/318,086, filed on Dec. 22, 2005, incorporated herein by reference in its entirety.

In one embodiment, the actuator 120 may be manually operated by maneuvering the actuator 120 from a site external to a body. The actuator 120 may include one or more features adapted for manual manipulation. For example, the actuator may include one or more looped elements adapted to be operated by fingers and/or thumb. The actuator 120 may advance the elongated member 150 distally by pushing on the actuator 120 by grasping the looped element and pushing it. The actuator 120 may be used to proximally draw the elongated member 150 by grasping and pulling of the looped element. In other embodiments, the actuator may be any means capable of advancing distally or pulling proximally the elongated member 150 coupled to the grasper 160.

The repositioning device 100 may further include an outer tube 130. The outer tube 130 also defines a lumen within which the inner tube 140 may be slidably disposed. In one embodiment, the outer tube 130 is an insertion tube of an endoscope. For example, if the repositioning device 100 is being used within the gastrointestinal tract, the endoscope may be a gastroscope, such as the Olympus GID Q160, 9.8 mm OD. The endoscope may permit the operator to view the removal or repositioning process of the implantable device and to manipulate the relevant features of both the repositioning device 100 and the implantable device during the removal or repositioning process. The positioning and movement of the endoscope may be accomplished by manually maneuvering the proximal end of the endoscope from a site external to the body.

Alternatively, the outer tube 130 may be a separate tube from an endoscope, wherein an endoscope may be place adjacent to the repositioning device 100 in order to view and manipulate the repositioning and/or removal process of the implantable device. The positioning of the outer tube 130 may be accomplished from a site external to the body. The positioning of the outer tube 130 may be manual, for example, by an operator maneuvering a proximal end of the outer tube 130.

In some embodiments, the repositioning device 100 may also include a retrieval hood 190. The retrieval hood 190 may be attached to a distal end of the outer tube 130. The retrieval hood 190 is adapted to capture at least a proximal portion of the implantable device. In some embodiments, the retrieval hood 190 is coupled to the outer tube 130 using an interference fit, where the diameter of the proximal end of the retrieval hood 190 is slightly larger than the distal end of the outer tube 130. In other embodiments, the retrieval hood 190 may be coupled to the outer tube 130 using alternative mechanical, chemical, or bonding techniques.

The retrieval hood 190 may generally be conical in shape. The retrieval hood 190 has openings at both a proximal end and a distal end. As shown, the distal end of the retrieval hood 190 may be flared to facilitate capture of an implantable device to be repositioned. In some embodiments, the retrieval hood 190 is made of a flexible material to facilitate its atraumatic placement within a body and to better accommodate at least the proximal portion of the implantable device prior to repositioning. The retrieval hood 190 may be made of a transparent, biocompatible rigid plastic such as polycarbonate or a flexible polymer such as polyurethane, PVC or silicone.

The additional visibility offered by the transparent retrieval hood 190 may be beneficial to the repositioning procedure. For example, if the repositioning device 100 is used through the working channel of an endoscope, (when the endoscope is the outer tube 130) the transparent retrieval hood 190 may allow for a wide field of view. Alternatively, a transparent retrieval hood 190 may also allow for easier viewing from an endoscope external to the repositioning device 100.

The repositioning device 100 may include a retrieval locking mechanism 195. In one embodiment, the retrieval locking mechanism 195 is a pincher-type lock. The retrieval locking mechanism 195, which is slideable upon the inner tube 140 is positioned at the proximal end of the outer tube 130, on the inner tube 140. Once the retrieval hood 190 is advanced over the implantable device to capture it, the pincher-type retrieval locking mechanism 195 is then pinched on the inner tube 140. The inner tube 140 with the elongated member 150 disposed therein is thus locked into place with respect to the outer tube 130 and the retrieval hood 190. This prevents inadvertent release of the radially-collapsed implantable device. In other embodiments, the inner tube 140 and elongated member 150 may be locked with respect to the retrieval hood 190 using other locking mechanisms such as compression locks, other screw-type locks, pincher-type locks, clamp-type locks or any means capable of locking the inner tube 140 and elongated member 150 in place.

The retrieval locking mechanism 195 is beneficial in preventing damage to surrounding tissue when the implantable device is removed or repositioned in the natural bodily lumen. If the inner tube 140 and elongated member 150 are not locked with respect to the retrieval hood 190, the implantable device captured within the retrieval hood 190 may release, thereby moving distal to the retrieval hood 190 allowing it to expand and exposing anchoring barbs to the tissues. Thus, when the implantable device is removed or repositioned within the natural bodily lumen, the exposed and expanded implantable device would be dragged within the natural bodily lumen, resulting in possible tissue damage.

Figure 2A:
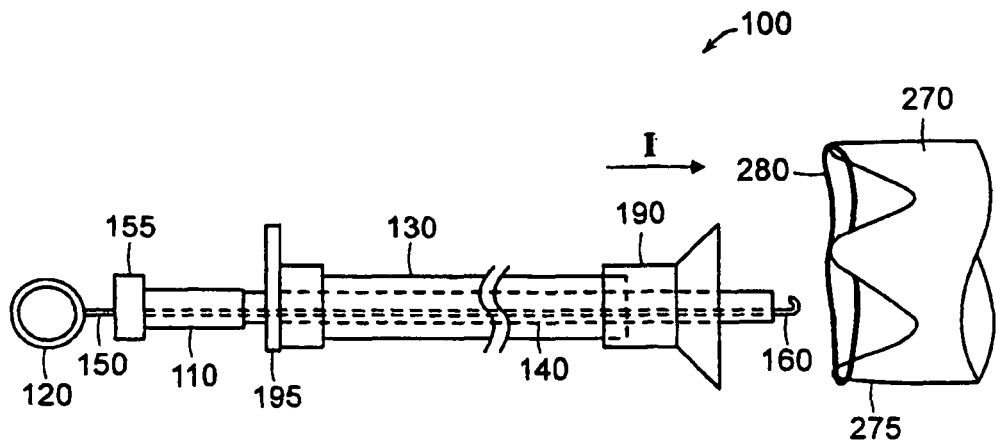
FIGS. 2A-2F are a series of schematic diagrams showing an exemplary embodiment of the invention capturing a proximal portion of an implantable device for repositioning.

A method of using the repositioning device 100 to capture at least a proximal portion of an implantable device 270 for repositioning and removal is shown in FIGS. 2A-2F. As shown in FIG. 2A, the grasper 160 coupled to the distal end of the elongated member 150, is advanced towards a drawstring 280 positioned on the proximal end of the implantable device 270 by pushing on the actuator 120 (as indicated by arrow I.) Details of the drawstring are shown in FIG. 11. The distal end of the grasper 160 can extend distally beyond the outer tube 130, the retrieval hood 190, and the inner tube 140.

Figure 2B:
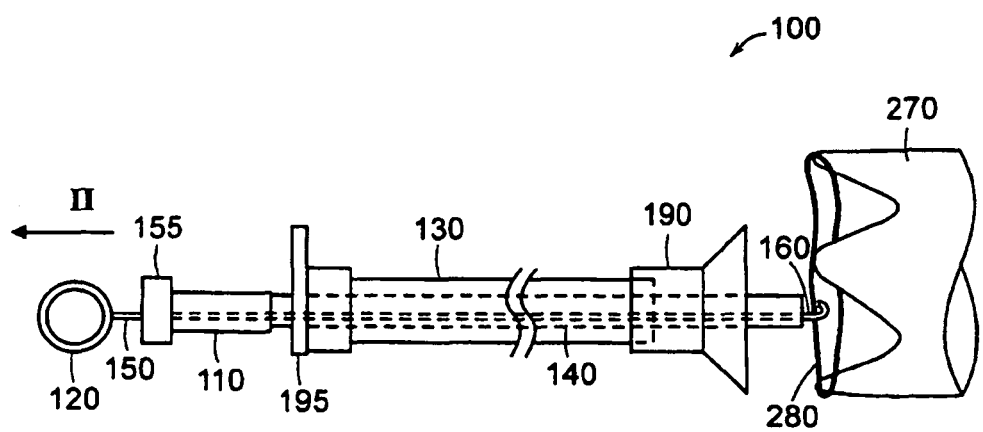

As shown in FIG. 2B, the grasper 160 extending distally beyond the inner tube 140, engages a portion of the drawstring 280 of the implantable device 270. The actuator 120 is then used to proximally draw the grasper 160 and the engaged portion of the drawstring 280 (as indicated by arrow II).

Figure 2C:
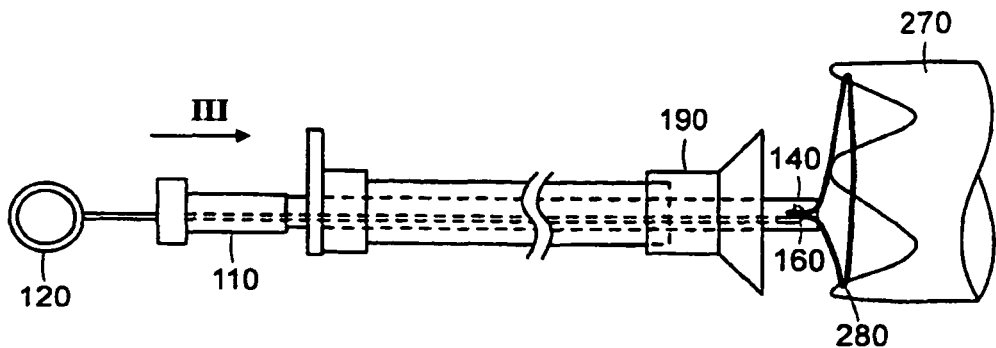

As shown in FIG. 2C, the grasper 160 and the engaged portion of the drawstring 280 are drawn proximally into the distal end of the inner tube 140, reducing slack in the drawstring 280. The inner tube 140 with the grasper 160 and the engaged drawstring 280 disposed in it distal end, is then advanced distally (indicated by the direction of arrow III). The distal advancement of the inner tube 140 may be accomplished by manipulating the handle 110 coupled to the inner tube 140.

Figure 2D:
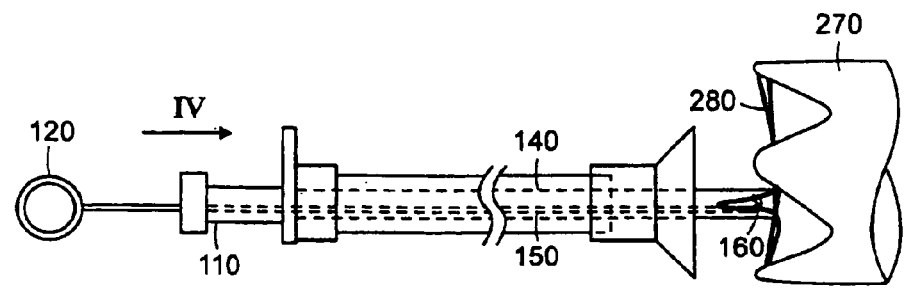

As shown in FIG. 2D, the inner tube 140 is advanced distally until it is within an interior portion of the implantable device 270, or beyond the proximal plane of the implantable device 270 (as indicated by arrow IV).

Figure 2E:
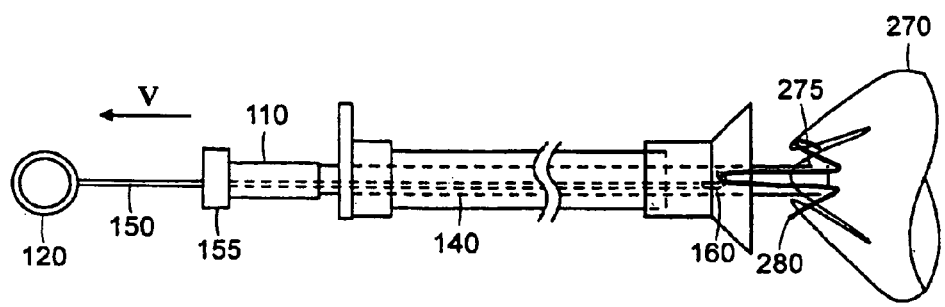

As shown in FIG. 2E, once the inner tube 140 is positioned within the interior of the implantable device 270, the actuator 120 is proximally pulled so that the grasper 160 coupled to the elongated member 150 pulls the engaged drawstring 280 proximally into the inner tube 140 (as indicated by arrow V). When the engaged drawstring 280 is pulled by the grasper 160, the engaged drawstring 280, is also drawn within the lumen of the inner tube 140 sufficiently to radially collapse the implantable device 270, thereby detaching it from the surrounding anatomy. For example, as previously described, some implants include an anchor or stent having barbs 275 adapted to pierce the surrounding muscular tissue of the intestine. As the drawstring 280 is withdrawn, the anchor or stent is collapsed radially until the barbs 275 are dislodged from the surrounding tissue. At least a proximal portion of the implantable device 270, is therefore radially collapsed.

The positioning of the inner tube 140 coupled to the grasper 160 within the interior of the implantable device 270, is advantageous in preventing damage to surrounding tissue within the natural bodily lumen. As the engaged drawstring 280 is pulled proximally into the inner tube 140, the implantable device 270 is radially collapsed, therefore avoiding significant axial pull on the drawstring 280. This avoids unnecessary dragging of the implantable device 270 through the natural bodily lumen, thus decreasing the chances of tissue damage cause by the exposed barbs 275.

Once the implantable device 270 has been sufficiently radially collapsed by the grasper 160, the elongated member 150 is locked into place by the grasper locking mechanism 155. The elongated member 150 is thus, no longer slideable within the inner tube 140 and the handle 110, but is fixed. The elongated member 150 remains fixed until the grasper locking mechanism 155 is unlocked.

Figure 2F:
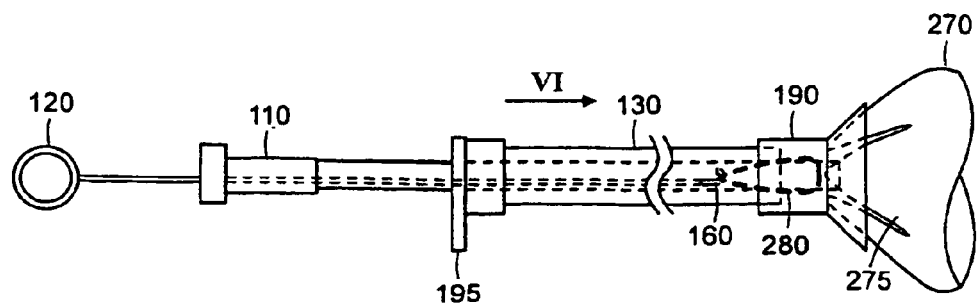

As shown in FIG. 2F, once the implantable device 270 is sufficiently collapsed and locked into place by the grasper locking mechanism 155, the outer tube 130 coupled to the retrieval hood 190 is advanced distally over the inner tube 140 and the radially-collapsed implantable device 270 (as indicated by arrow VI). As the retrieval hood 190 is advanced, it preferably captures at least a proximal portion of the implantable device 270. If the outer tube 130 is an insertion tube of an endoscope, the proximal portion of the endoscope may be manually maneuvered from a site outside of the body in order to centralize the collapsed implantable device 270 within the flared distal end of the retrieval hood 190. Similarly, if the outer tube 130 is a tube distinct from an endoscope, such as a catheter, the proximal end of the outer tube 130 may be maneuvered manually and/or from a site external to the body.

Advancing the retrieval hood 190 over the implantable device 270 may be advantageous in avoiding damage to surrounding tissue. Because the retrieval hood 190 is being advanced over the implantable device 270, at least proximally facing collapsed barbs 275 are covered and will not traumatize the tissue within the natural bodily lumen. The distal facing barbs 275, even if left uncovered will not penetrate into the tissue as they are facing opposite to the direction of withdrawal (indicated by arrow V) and therefore will not cause damage to surrounding tissue. This facilitates the safe removal or repositioning of the implantable device 270 within the natural bodily lumen.

Figure 3A:
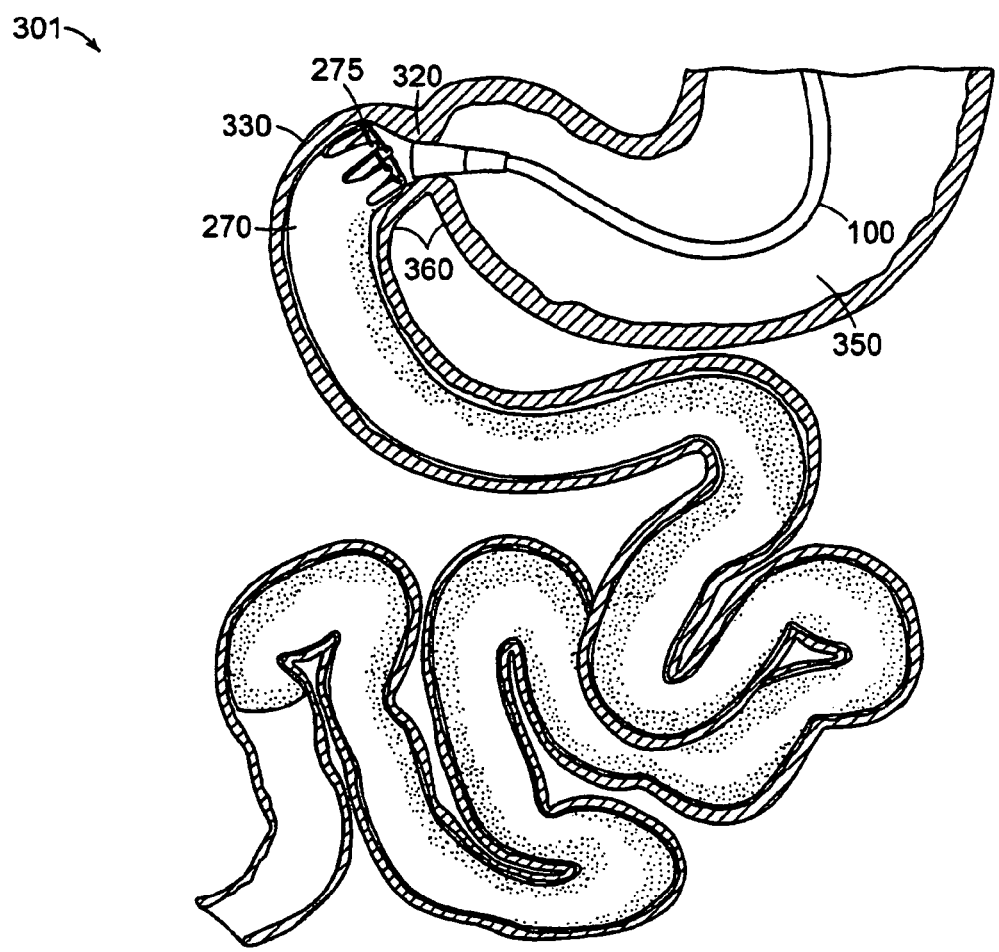
FIGS. 3A-3F are another series of schematic diagrams showing an exemplary embodiment of the invention retrieving an implantable device in the intestine.
Figure 3B:
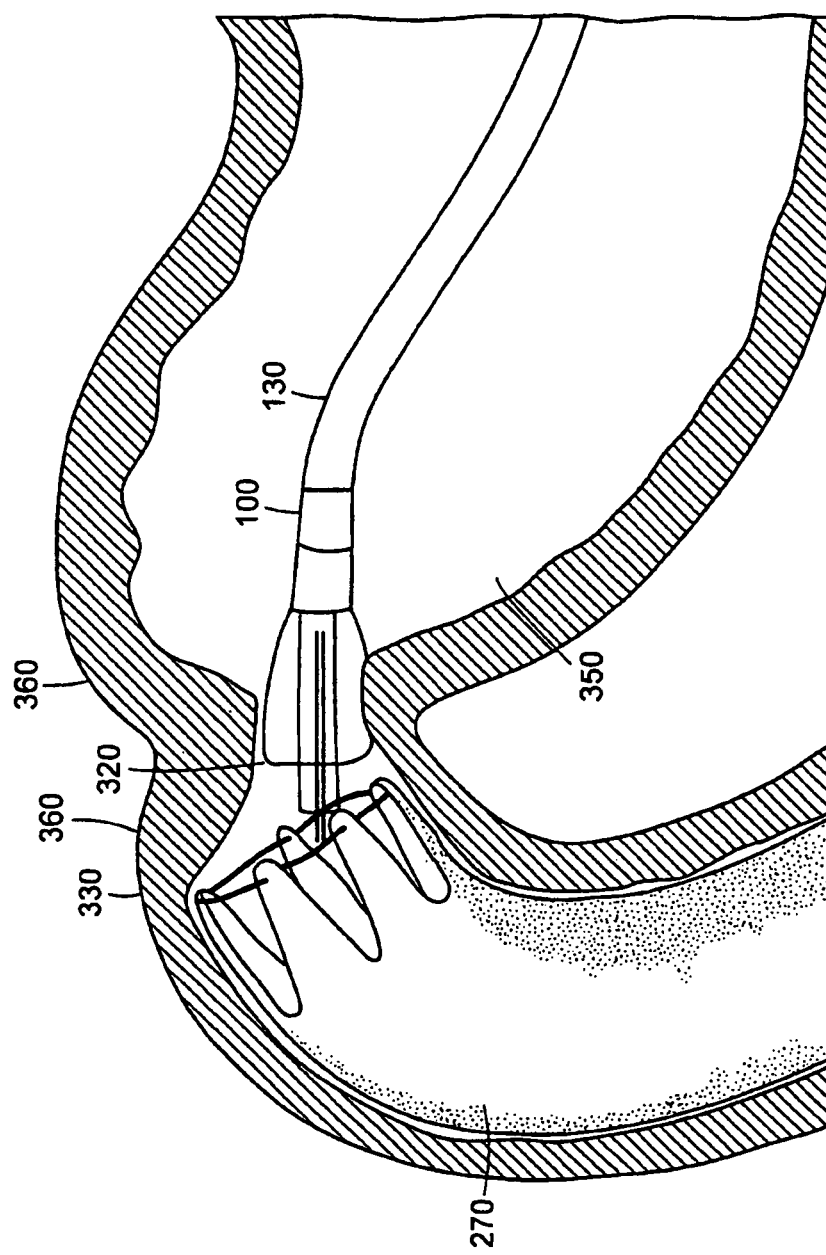

Once the retrieval hood 190 adequately captures the collapsed implantable device 270, the inner tube 140 and elongated member 150 are locked with respect to the retrieval hood 190 using the retrieval locking mechanism 195, thereby preventing the inadvertent release the implantable device 270 and thereby exposing barbs 275. Once captured and locked into place, the repositioning device 100 and the implantable device 270 can be safely removed from the body or repositioned within the natural bodily lumen as one unit. Another illustration of the removal process is presented in FIGS. 3A-3F for an application within a gastrointestinal tract 301. The implantable device 270 is secured or attached in the pyloric region 360 of the stomach 350 or, as shown in FIG. 3A, just distal to the pylorus 320 in the proximal portion of the duodenum 330. As shown in FIG. 3B, the repositioning device 100 is advanced distally from the outside of a body through the esophagus (not shown) and further through the stomach 350 and the pyloric region 360 of the stomach 350 in order to reach the proximal portion of the implantable device 270. Preferably, a distal portion of the repositioning device 100 is advanced through the pyloric sphincter 320 extending at least partially into the proximal duodenum 330.

Figure 3C:
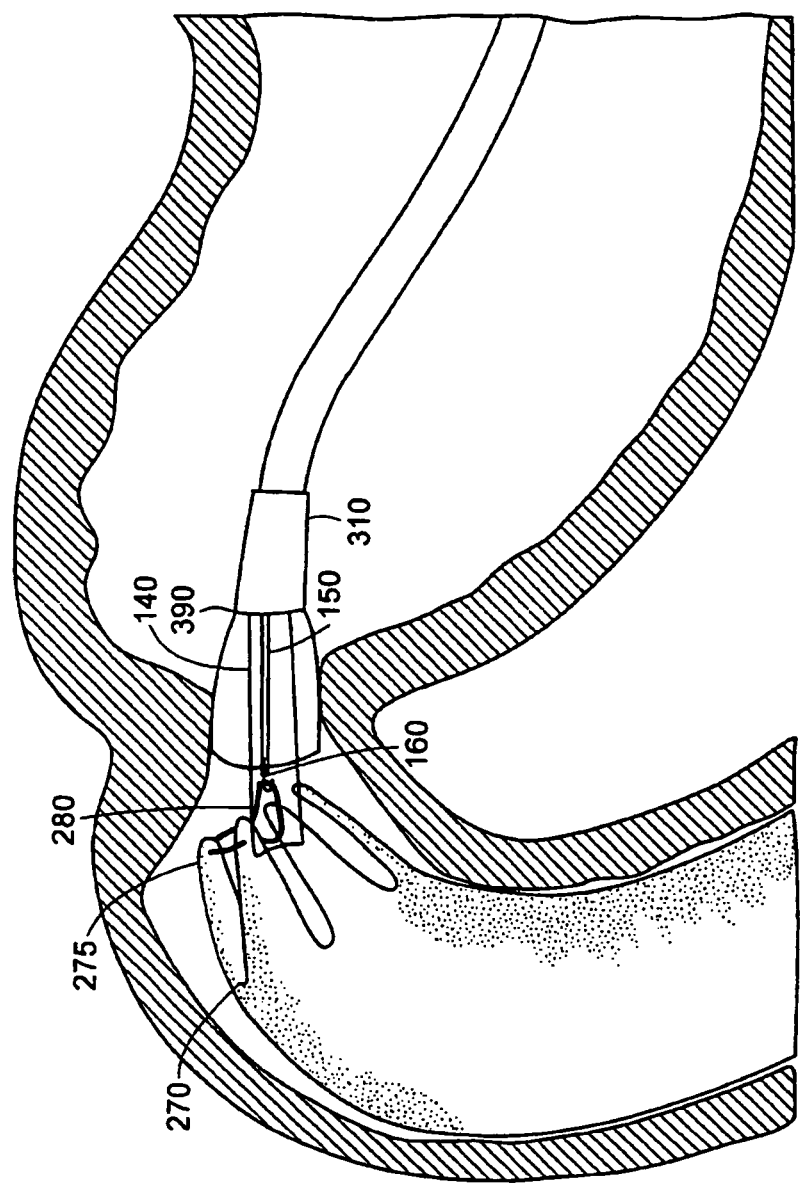

As shown in FIG. 3C, the inner tube 140 with the grasper 160 and the engaged drawstring 280 disposed within the distal end of the inner tube 140, is advanced distally until it is within the interior, or beyond the proximal plane of the implantable device 270. The grasper 160, can then be pulled proximally operating the drawstring 280, thereby radially collapsing a proximal portion of the implantable device 270. The barbs 275 of the implantable device 270 are dislodged from the surrounding tissue. Once the implantable device 270 is sufficiently collapsed, the elongated member 150 coupled to the grasper 160 can be locked into place by locking the grasper locking mechanism (not shown) in order to prevent release of the collapsed implantable device 270.

Figure 3D:
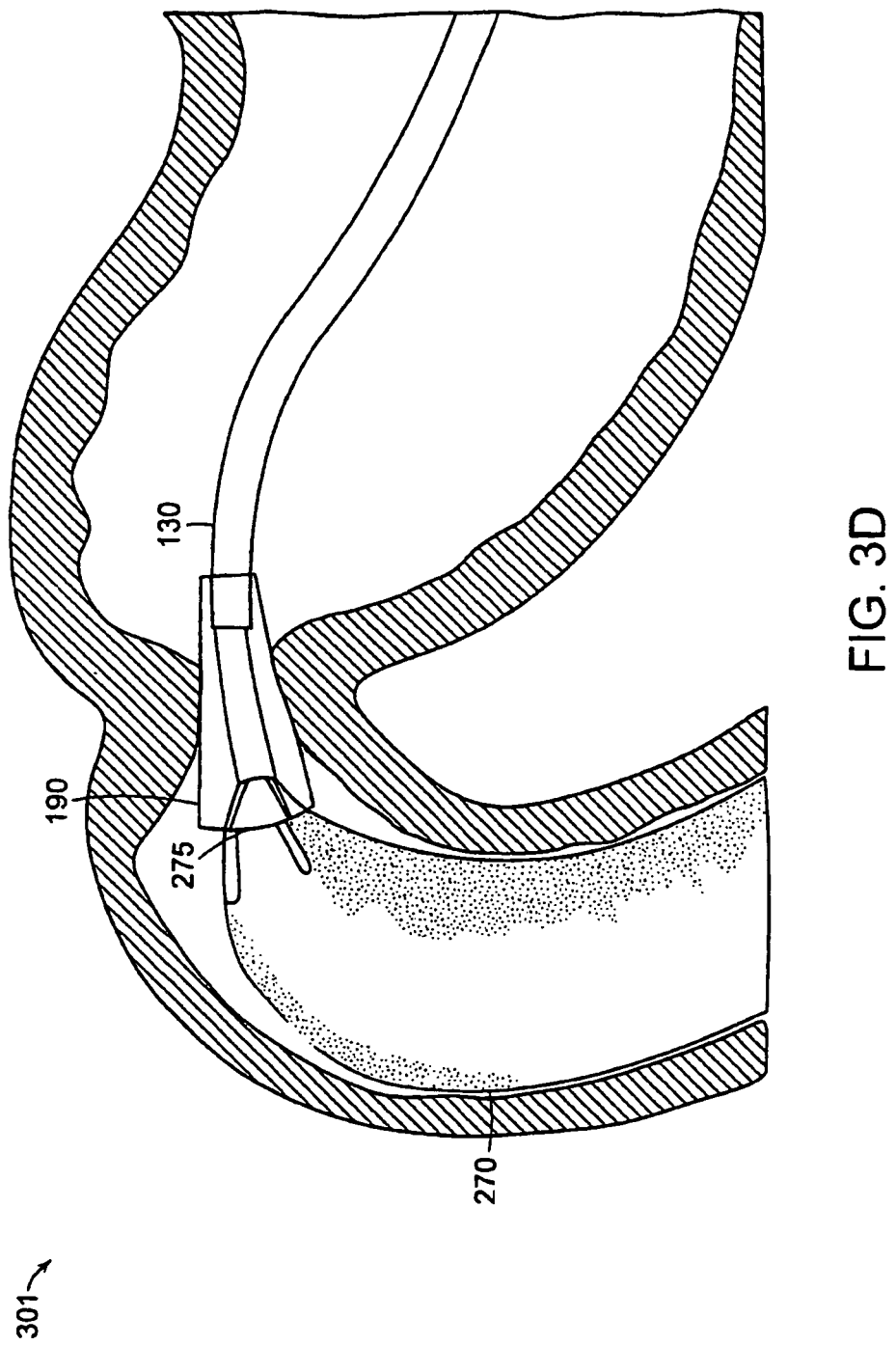

As shown in FIG. 3D, once the implantable device 270 has been radially collapsed, the outer tube 130 coupled to the retrieval hood 190 is advanced distally in order to capture a collapsed proximal portion of the implantable device 270 and the dislodged barbs 275. If the outer tube 130 is the insertion tube of an endoscope, the proximal portion of the endoscope may be maneuvered from a site external to the body in order to center the collapsed implantable device 270 and collapsed barbs 275 within the flared head of the retrieval hood 190. For example, the endoscope may be a gastroscope, such the Olympus GID Q160, 9.8 mm OD.

Similarly, if the outer tube 130 is a tube distinct from an endoscope, the proximal portion may be maneuvered to centralize the collapsed implantable device 270 and the dislodged, collapsed barbs 275 within the flared end of the retrieval hood 190. The centralization within the retrieval hood 190, which promotes a complete capture of the proximal end of the collapsed implantable device 270 and the collapsed barbs 275 by the retrieval hood 190, reduces the chances of damage to the surrounding tissue, which may be caused by protruding barbs 275 from the retrieval hood 190, when the implantable device 270 and the repositioning devices 100 are removed from the body by being drawn proximally through the gastrointestinal tract 301 and esophagus.

Figure 3E:
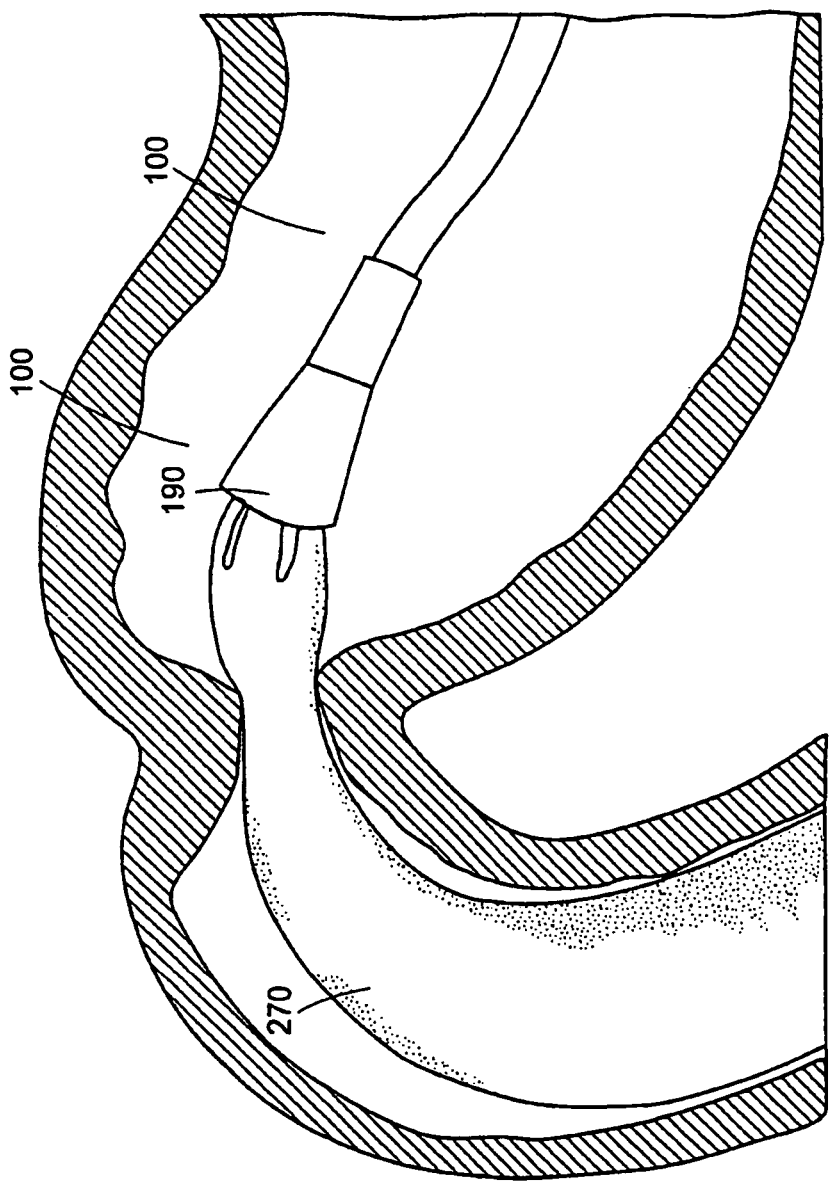
Figure 3F:
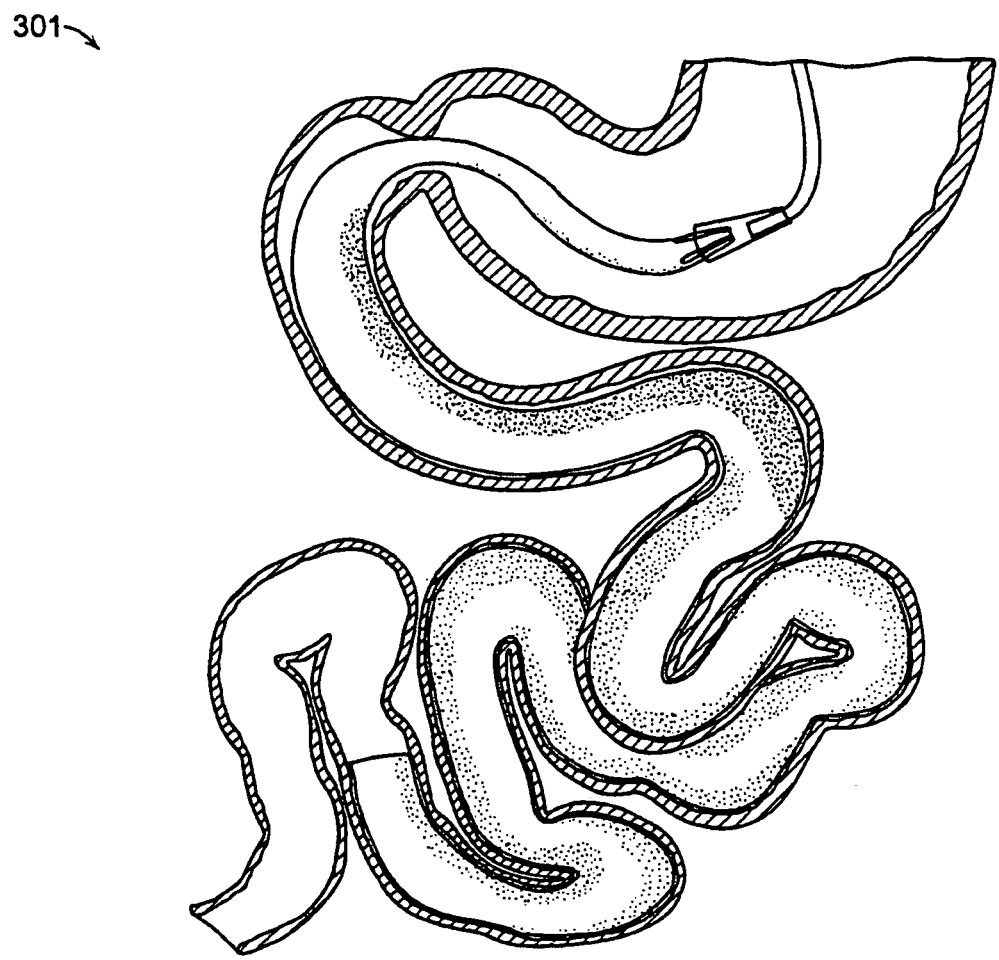

Once effectively captured in the retrieval hood 190 and locked in place by the retrieval locking device, the implantable device 270 and the repositioning device 100 may be repositioned to a different location within the gastrointestinal tract 301 or removed from the body as one unit as shown in FIGS. 3E and 3F. When removing an implantable device, this unit is proximally drawn through the esophagus in a safe manner.

Alternative embodiments are shown in FIGS. 4A and 4B, where the repositioning device 100 includes a rotary actuator 410. The rotary actuator 410 can be used to collapse the implantable device. The rotary actuated device 100 may similarly include the inner tube 140, the elongated member 150 and a grasper 450. Once the grasper 450 captures a portion of the drawstring of the implantable device, a rotary actuator 410 spins the grasper 450 causing the drawstring to wind about the grasper 450. In one embodiment, the grasper 450 may be a spade with a notch as shown in FIG. 4B. In other embodiments, the grasper 450 may be a hook or any means capable of engaging the drawstring. For example, the distal end of the elongated member 150 can be shaped to form a hook as shown in FIG. 4A.

The winding action causes the drawstring to wrap about the grasper 450, thereby operating the drawstring and radially collapsing the implantable device. Once the implantable device has been radially collapsed the proximal portion of the implantable device can be captured by a retrieval hood when provided as previously described. The entire device 100 and the implantable device may then be removed in a similar manner to that described in FIGS. 3A-3F.

An advantage provided by the rotational device is that it is not stroke-length limited. Stroke-length refers to the length of translation provided by the grasper within the inner tube. This translation may be limited by the physical dimensions of the device and will limit the length of drawstring that can be withdrawn into the sleeve. There is no similar limitation to the amount of rotation (i.e., number of turns). As long as the hook and wire are capable of rotating, the number of rotations can be varied to selectably wind a desired length of the drawstring about the wire.

It may be possible that with a fixed stroke length, if the drawstring on the anchor stretches, the grasper may not be able to fully collapse the anchor. Additionally, much of the force applied at the proximal end of the reciprocating device may be lost through the shaft as the shaft buckles. Almost all of the torque provided at the proximal end of the rotational device can be delivered to its distal end while keeping it flexible. Also, the actuation of the rotational device may provide improved ergonomics, since it is translated separately from its rotational motion. This may make it easier to move the drawstring collapse point proximal or distal to dislodge the anchor or stent, while keeping the drawstring collapsed.

An alternative type of grasper is shown in FIG. 5, where the grasper is a rat-tooth type grasper 510. The rat tooth grasper 510 is advanced within the interior of the drawstring as described in previous figures. The rat tooth grasper 510 is then actuated so that its jaws 520 grasp the drawstring between the two jaws 520. The rat tooth grasper 510 is advantageous in that the drawstring is easily released if desired by simply opening the jaws 520 of the rat tooth grasper 510. The jaws 520 are opened by advancing distally the jaws 520 until they exit the inner tube 140. The jaws 520 are closed by pulling the jaws into the inner tube 140.

An alternative grasper is also shown in FIG. 8A. The retrieval grasper 800 includes hooks 810. The grasper also includes first extensions 820 and dog legs 830. The dog legs 830 are angled out 12 degrees from parallel with the extension 820. The hooks 810 are made with a 150 degree arch sweep. As shown in FIG. 8B, the first extensions 820 stay parallel to a sheath 840 when retracted into the sheath 840, and the dog legs 830 prevent the hooks 810 from engaging the edge of the sheath 840. This type of grasper is further described in U.S. Provisional Application 60/902,924, filed on Feb. 22, 2007, herein incorporated by reference in its entirety.

Figure 6A:
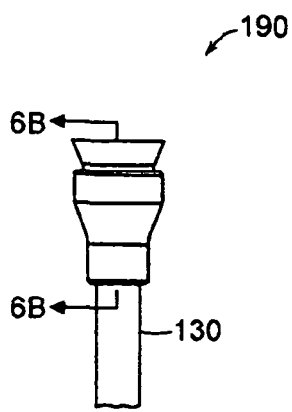
FIGS. 6A-6C show an alternative embodiment of a retrieval hood.
Figure 6B:
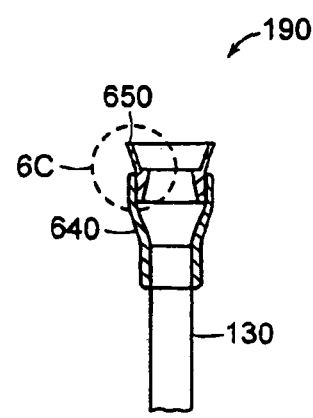
Figure 6C:
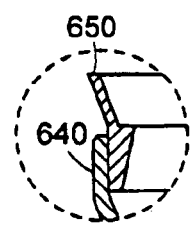

An alternative or additional embodiment of the repositioning device 100 is show in FIG. 6A-6C, wherein the retrieval hood 190 includes a feature adapted to steer the grasper towards the center of the implanted device. As shown in the cross section in 6B and 6C, an interior ramp 640 is provided over at least a portion of the interior of the retrieval hood 190. Additionally, the retrieval hood 190 includes a flared end 650. The proximal end of the retrieval hood 190 may be coupled to the outer tube 130 or alternatively, to the distal end of an insertion tube of an endoscope.

For example, the angle of the flared end 650 can extend over about 10 to 90 degrees about the interior of the retrieval hood 190 as shown in FIG. 6B. The interior ramp 640 is aligned to centrally position the distal end of the inner tube 140 with the grasper 160 and engaged drawstring 280 disposed therein, within the interior of the implantable device prior to and as it is radially collapsing the device. This may be advantageous, because the inner tube 140 and grasper 160 tend to be eccentric, or biased towards one side since the working channel of the endoscope through which the grasper is positioned is eccentric. Distal advancement of the inner tube 140 through the retrieval hood 190 towards the implanted device, allows the inner tube 140 and elongated member 150 to bend towards a central position within the drawstring of the implantable device, and pull the drawstring. This allows for primarily uniform radial force to be applied to the drawstring in order to radially collapse the implantable device.

As the retrieval hood 190 is advanced distally to capture the radially collapsed device, the interior ramp 640 along with the angle of the flared end 650 allows the elongated member along with the radially collapsed implantable device to be centralized within the retrieval hood 190, therefore facilitating the removal or repositioning of the implantable device.

Figure 7A:
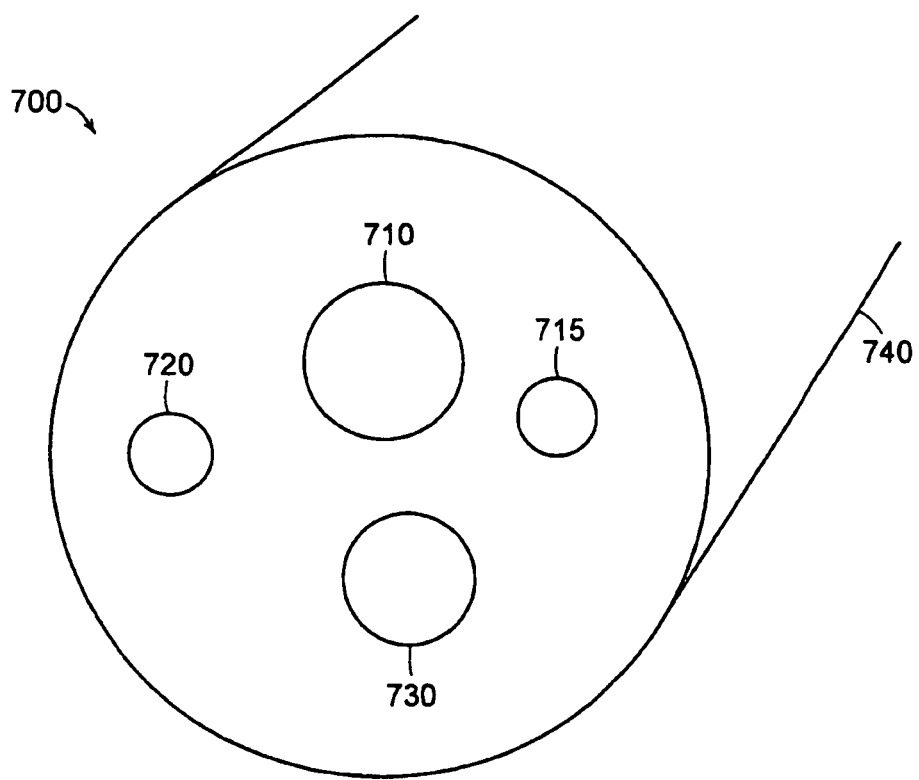
FIGS. 7A and 7B show an endoscope used to view the repositioning process.
Figure 7B:
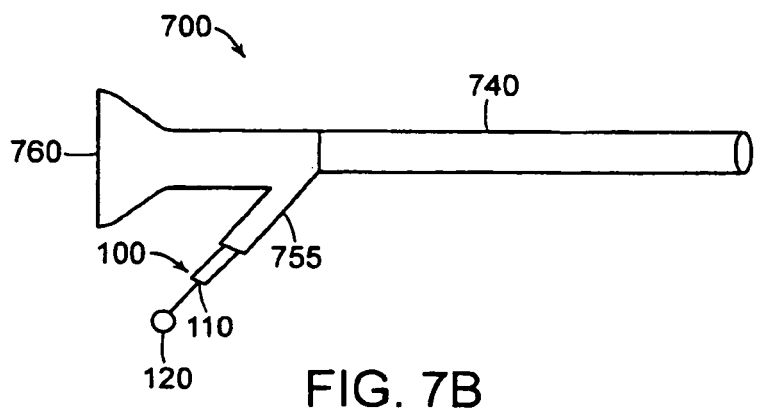

As shown in FIGS. 7A and 7B, all procedures just described can be observed by the endoscopist using an endoscope and camera. Such a visual aid will facilitate operation of the proximal controls (e.g., handle 110 and actuator 120) to position the grasper 160 near the drawstring, to engage the drawstring, to position the inner tube 140 within the interior of the implantable device so that the implantable device may be sufficiently collapsed, to confirm that the barbs are sufficiently detached, and to capture the proximal end of the implant with the retrieval hood 190. Beneficially, the retrieval hood 190 can be formed of a transparent material, such as polycarbonate, PVC or polyurethane. Such additional visibility offered by the transparent retrieval hood 190 is advantageous to the removal procedure, by allowing clear viewing of the repositioning procedure.

As shown in FIG. 7A, the distal end of the endoscope 700 includes an objective lens 710, through which the repositioning procedure can be viewed. A light source 720 may be provided to enable brighter viewing of the repositioning procedure. An irrigation port 715 may also be provided. Additionally, the distal end of the endoscope 700 may include an instrument channel outlet 730.

As described in previous figures, the outer tube 130 may be the insertion tube 740 of the endoscope 700 as shown in FIG. 7B. The distal end of the insertion tube 740 of the endoscope 700 may include the instrument channel outlet 730, as shown in FIG. 7A. The inner tube 140 is slidably disposed within the insertion tube 740 of the endoscope 700, and may be distally advanced or proximally pulled through the instrument channel outlet 730. The proximal end of an instrument channel 755 is shown. The actuator 120 and handle 110 of the repositioning device 100 may be maneuvered from the instrument channel 755, through which the inner tube 140 of the repositioning device 100 is slidably disposed. The procedure may be viewed and directed by an endoscopist, for example, looking through an eyepiece 760 or at an image projected on a monitor.

Alternatively, the outer tube 130 may be a distinct tube from the insertion tube 740 of the endoscope 700. In this case, if the operator wishes to view the repositioning procedure through the endoscope 700, the endoscope 700 may be positioned adjacent to the repositioning device 100 within the natural bodily lumen. The viewing and/or guiding of the repositioning procedure is facilitated by the transparent retrieval hood 190.

An endoscope may be used in combination with, or independent of a fluoroscope. Alternatively, fluoroscopy may be utilized to guide and view the repositioning procedure independent of endoscopy.

Fluoroscopy may be used to guide the removal or repositioning of an implantable device. The distal end of the inner tube 140 may be marked with a radiopaque marker. Fluoroscopy may be used to confirm that the distal end of the inner tube 140 is positioned within the interior of the implantable device. If the inner tube 140 is not properly positioned, the radiopaque marker facilitates viewing of the distal end of the inner tube 140 and thus adjustment of the inner tube 140 to sufficiently radially collapse the implantable device.

Alternatively, or in addition, a combination of radiopaque markers may be provided on the repositioning device 100 as well as on the implantable device. This may particularly be useful if one wishes to utilize fluoroscopy independent of an endoscope. For example, a portion of the drawstring of the implantable device may be marked with a radiopaque marker. The grasper 160 or elongated member 150 may be marked with a radiopaque marker. In this way, an endoscope may not be required, as the entire repositioning procedure and the relevant parts which need to be guided during the repositioning procedure, are sufficiently displayed on a monitor.

Figure 9A:
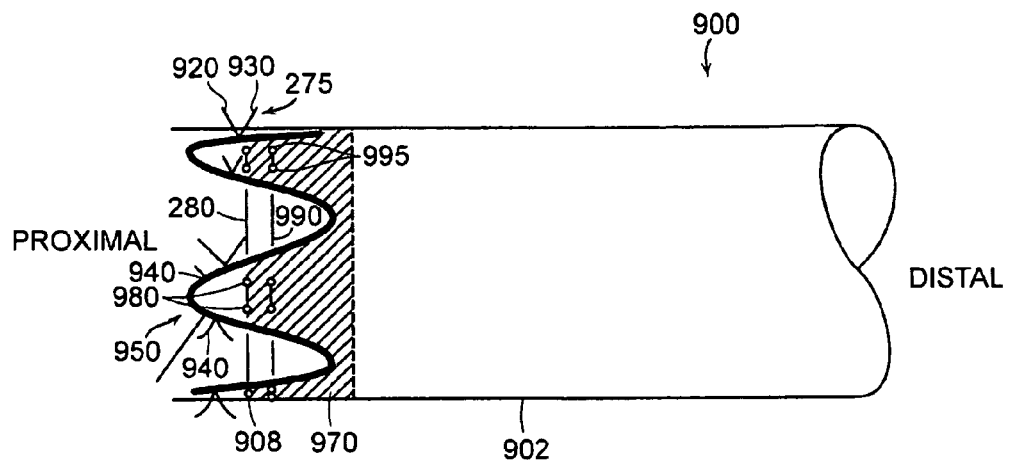
FIG. 9A illustrates an embodiment of a gastrointestinal device with a wave anchor and drawstrings.

FIG. 9A is a side view of a gastrointestinal implant device 900. The gastrointestinal implant device 900 includes an elongated, open-ended, unsupported flexible sleeve or tube 902 having a first proximal opening and a second distal opening. Within the sleeve 902 is a passageway that extends from the first proximal opening to the second distal opening for transporting the chyme exiting the stomach. The surface of the passageway (the interior surface of the implant device 900) is smooth to enable the chyme to easily pass through.

The exterior surface of the implant device 900 is smooth to prevent tissue in-growth and to be non-irritating to the bowel.

The sleeve material 902 is floppy, thin, and conformable so that it collapses in the intestine to a small volume to minimize bowel irritability. Also, the sleeve 902 has minimal hoop strength, so that it can fall flat until food passes through, thus minimizing interference with peristalsis. It has a low coefficient of friction (less than about 0.20) so that chyme slides easily through it and the bowel slides easily around it. Further, the low coefficient of friction prevents the sleeve from sticking to itself, thus making it easier for the sleeve 902 to open as chyme is pushed through it. It is of low permeability to fluids so that the chyme does not touch the bowel wall and the digestive enzymes do not significantly breakdown the chyme. It is biologically inert and non-irritating to the tissues. One class of materials includes fluoropolymers. In some embodiments, the sleeve 902 is formed from expanded PTFE with a wall thickness of about 0.0005 to 0.001 inches and an internodal distance of 20 microns. This material is hydrophobic but is slightly porous. However, these very small pores may plug over time. The porosity may be reduced by coating the material on the inside, outside or in the pores with dilute solutions of silicone or polyurethane.

Another material is polyethylene with a wall thickness of less than 0.001 inches. Other materials include Cast PolyTetraFluoroEthylene (PTFE, e.g., TEFLON™), Cast PTFE with Fluorinated Ethylene Propylene (FEP) or PerFluoroAlkoxy (PFA) coating to minimize pin holes, Extruded FEP and Extruded PFA. These materials are solid and substantially non-porous in contrast to ePTFE which is porous, but these materials are also considered to be fluoropolymers. The wall thickness is preferably less than about 0.001 inches. Rubber-like materials typically have friction coefficients of about 1-4, significantly stickier than these materials. However, in alternate embodiments other materials having similar characteristics can be used.

In some embodiments, the sleeve 902 is formed using a combination of two or more materials. For example, the sleeve 902 can be formed using a combination of ePTFE and FEP. Such a combination can be formed by layering the two materials together and generally provides a low coefficient of friction while being substantially non-permeable. The ePTFE provides significant flexibility and softness while the FEP is used to seal the pores in the ePTFE making the material substantially non-porous. This material is used to form the sleeve as well as to cover both the outer and inner surfaces of the anchor.

The sleeve 902 includes two layers of material at least at the proximal end. A first outer layer covers the exterior of the anchor 908. The second inner layer covers the interior surface of the anchor 908. The barbs 275 protrude from the exterior surface of the anchor 908 through the first outer layer of the sleeve 902. The holes in the first outer layer through which the barbs 275 protrude can be filled with an impervious material such as silicone or urethane to limit mixing of digestive juices with the chyme flowing through the passageway. The diameter of the sleeve 902 is selected such that the first outer layer of the sleeve 902 fits over the anchor 908.

The sleeve length is variable and can range from about one foot to about five feet. The typical length of the sleeve 902 is about 2 to 4 feet measured from the anchor (barbs 275) in the bulbous duodenum to below the ligament of Treitz. The length 912 of the sleeve 902 is selected to bypass the duodenum and a portion of the jejunum. The length can optionally be increased to further decrease absorption by bypassing a longer section of the jejunum. Thus, the length of the sleeve 902 is variable and may be dependent on the patient's Body Mass Index (BMI). The procedure is a less invasive alternative to surgery for the treatment of obesity and morbid obesity and also provides a new treatment approach for Type-2 diabetes.

Within the implant device 900 at the proximal end including the first proximal opening is a collapsible self-expanding anchor 908. The anchor 908 may be a collapsible self-expanding stent with struts. Alternatively, the anchor 908 may be a collapsible, self-expanding wave type anchor coupled to the proximal portion of the sleeve 902 as shown here. The wave anchor 908 includes adjacent interconnected struts 940 connected by wave peak 950. In one embodiment, the anchor 908 has ten struts.

The wave anchor 908 includes a compliant, radial spring shaped into an annular wave pattern, providing an outward radial force, while allowing substantial flexure about its perimeter. Such flexure is advantageous as it allows for minimally-invasive delivery and ensures that the device will substantially conform to the surrounding anatomical structure when implanted. The annular wave element can be formed from one or more elongated resilient members and defines a lumen along its central axis formed between two open ends. When implanted, the central axis of the anchor 908 is substantially aligned with the central axis of the duodenum, allowing chyme to pass through the device 900. Additionally, the compliant wave anchor 908 minimizes trauma to the tissue by providing sufficient flexibility and compliance, while minimizing the likelihood of tissue erosion and providing a solid anchoring point to the tissue.

The compliant wave anchor 908 can be manufactured from a resilient metal such as a heat-treated spring steel, stainless steel, or from an alloy such as NiTi alloy commonly referred to as Nitinol. Other alloys include nickel-cobalt-chromium-molybdenum alloys possessing a unique combination of ultrahigh tensile strength, such as MP35N. Additionally, the wave anchor 908 can be formed from a polymer and/or a composite having similar properties. The wave anchor 908 can be manufactured from a single strand, such as a wire, contoured into the desired shape. Alternatively, the wave anchor 908 can be manufactured from multi-strands of the same or different materials similarly contoured to the desired shape. In some embodiments, the wave anchor 908 can be cut into the wave shape from tubular stock of the desired material, such as Nitinol. The wave anchor 908 can be removably attached within the body using any of the methods described herein for securing a anchor 908, including the use of barbs 275 attached to, and/or formed on the anchor itself. Preferably, the anchor 908 is radially collapsible for endoscopic insertion.

The wave anchor 908 includes webbing material 970 between the struts 940 of the anchor 908. The webbing material 970 can be made of a class of materials including fluoropolymers. In some embodiments, the webbing material 970 is formed from expanded PTFE. Another material is polyethylene. Other materials include Cast PolyTetraFluoroEthylene (PTFE, e.g., TEFLON™), Cast PTFE with Fluorinated Ethylene Propylene (FEP) or PerFluoroAlkoxy (PFA), Extruded FEP and Extruded PFA. Wave anchors are further described in U.S. application Ser. No. 11/299,392, filed on Sep. 16, 2005, claiming the benefit of U.S. Provisional Application 60/611,038 filed on Sep. 17, 2004, herein incorporated by reference in their entireties.

The anchor 908 includes a plurality of opposed barbs 275 for anchoring the implant device 900 to the muscular tissue of the duodenum. The barbs 275 include pairs of rigid, elongated barbs. Each side of the pair, respectively side 920 and side 930 are outwardly directed at fixed angles and in opposite axial directions. The barbs are of a length such that they are able to penetrate muscular tissue.

Figure 12A:
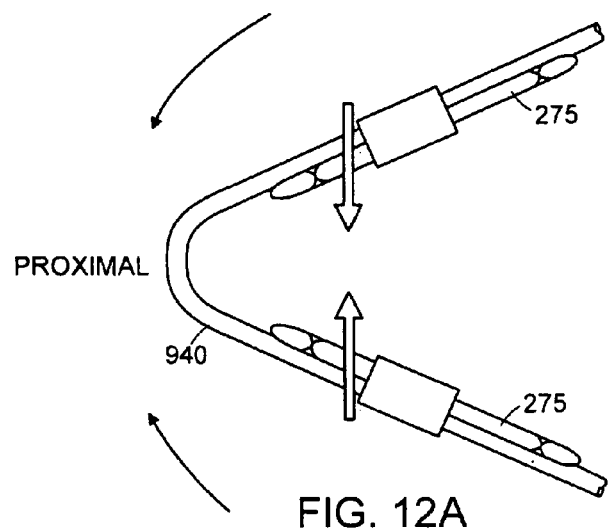
Figure 12B:
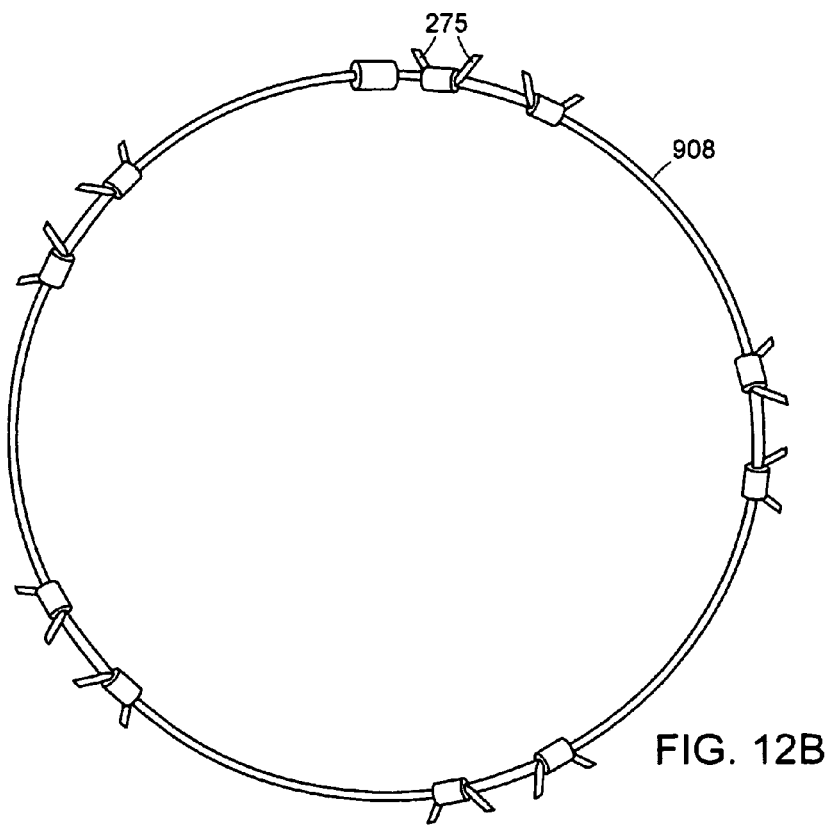

Further details of the barbs 275 are shown in FIGS. 12A-12D. Each of the struts 940 has one set of barbs with both proximal and distal facing points. The barbs 275 are made from a single piece of wire and are crimped onto each strut 940 with a piece of stainless steel tubing. The barbs 275 are located at the proximal end of the anchor 908. Each barb 275 is crimped such that the barb 940 is located on the inside of each strut 940 as shown in FIG. 12, that is, on the side facing the adjacent strut intersecting at the proximal end. This minimizes the likelihood of getting adjacent struts 940 intersecting at the distal ends hooked onto the barbs 275 during delivery when the anchor 908 is collapsed. An end-on view of the anchor 908 with barbs 275 is shown in FIG. 12B. A side view of the anchor 908 with barbs 275 is shown in FIG. 12C.

As shown in FIG. 12D, the proximally facing barbs 1220 are at least 2.0 mm (0.080 inches) in height off the strut 940. The distal facing barbs 1210 protrude at least 2.5 mm (0.10 inches) in height. If the barbs 275 are shortened below roughly 1.5 mm, the implant migrates quickly. In one embodiment, the proximal facing barbs 1220 are short so as to make it easy to remove the device from the surrounding tissue, and to cover the barbs 275 in the hood 190 as the device is removed from the body.

The distal facing barbs 1210 may be longer. Even though peristalsis moves the implant in both directions, the overriding force is to pull the implant distal, thus the distal barbs need to be longer to hold the device in place within the muscle. The distal facing barbs 1210 may be up to 6 mm in height. There is a risk as they are made longer that they may penetrate organs that are adjacent to the duodenum such as the liver or pancreas.

The uncompressed duodenal tissues are about 3 mm thick. When an anchor is placed in the duodenum, the inner diameter of the duodenum expands to accommodate the anchor. As the inner wall expands, the duodenal wall thins to 1 to 2 mm in thickness. Therefore, proximal or distal barbs with a height higher than 2.0 mm may be useful to ensure that they penetrate the muscularis. The reason barbs may be desired to have a height greater than 2 mm is that the wall of the duodenum will thicken over time so that a shorter barb will end up further from the muscular wall. Piercing beyond the muscle layer is not inherently dangerous; omentum from the stomach area will tend to cover over and seal any sites of penetration very quickly. Additionally, inflammatory cells will invade the area to seal off any sites where penetration of the muscle wall has occurred.

The barbs 275 are made of 0.020 inch diameter, nitinol wire making them quite stiff. The barbs are stiff enough to not be deflected by the soft tissues within the gastrointestinal tract. It takes about 1 lb of force per barb to deflect from 40 degrees to 90 degrees. The range of diameters that could be effectively utilized in nitinol would be 0.005" to about 0.030". Any diameter smaller than 0.005" results in a floppy barb that does not resist deflection well. Beyond a diameter of 0.030", barbs are so stiff that collapsing the anchor into a small tube for delivery becomes exceeding difficult.

They are made of nitinol to facilitate elastic bending when they are loaded into the delivery capsule. The angle of each barb 275 to the anchor strut 940 is about 40 degrees. This angle could vary from about 20 degrees to about 90 degrees.

The diameter of the anchor 908 is dependent on the diameter of the duodenum, that is about 1.0" to 2.5" based on human anatomy variations. The anchor is adapted to be retained within the duodenum, particularly in the duodenal bulb just distal to the pylorus. In one embodiment, the length of 1 inch of the anchor 908 is selected to reside within the bulbous duodenum. In the current embodiment, the length of the anchor is 32 mm while the relaxed diameter is 53 mm.

The intraluminal anchor can also include the drawstring 280 as previously described, to facilitate repositioning and/or removal. The drawstring 280 can be provided at a proximal end of the implant device 900 and be adapted for engagement by a removal device such as a hook. The drawstring 280, when engaged, can be pushed or pulled by the removal device, in opposition to the stationary intraluminal anchor, to at least partially collapse at least part of the intraluminal anchor. With a reduced diameter, the device can be removed through, or repositioned within, the natural bodily lumen. In some embodiments, at least a portion of the device is drawn into a retrieval hood, sheath, or overtube prior to removal as shown in FIGS. 2A-2F.

The drawstring 280 is shown woven through pairs of eyelets 980 distal to the wave peak 950 in the webbing material 970. The implantable device 900 can also include a second drawstring 990 distal to drawstring 280. This drawstring can also be woven through pairs of eyelets 995 distal to eyelets 980 for drawstring 280. The second drawstring 990 is an alternative drawstring in the situation that the first drawstring 280 breaks during repositioning or removal.

Figure 9B:
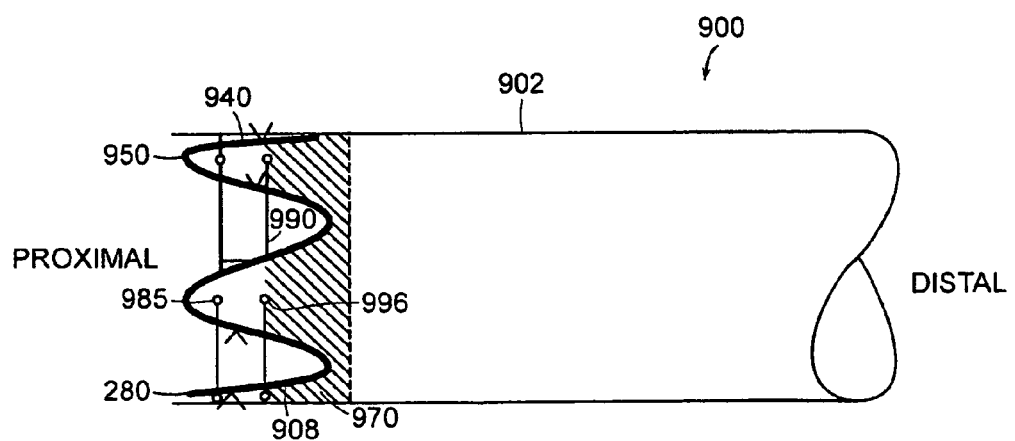
FIG. 9B-9D shows an alternative embodiment of the gastrointestinal implant device of FIG. 9A.

FIG. 9B illustrates an alternative embodiment of the weaving of the drawstrings 280 and 990. The drawstring 280 is woven through a single eyelet 985 in the webbing material 970, and over and under respective struts 940. The second distal drawstring 990 can be threaded through pairs of eyelets 995 as described in FIG. 9A or alternatively can also be threaded through an additional single hole 996 distal to the hole 985 for the drawstring 280.

Figure 9C:
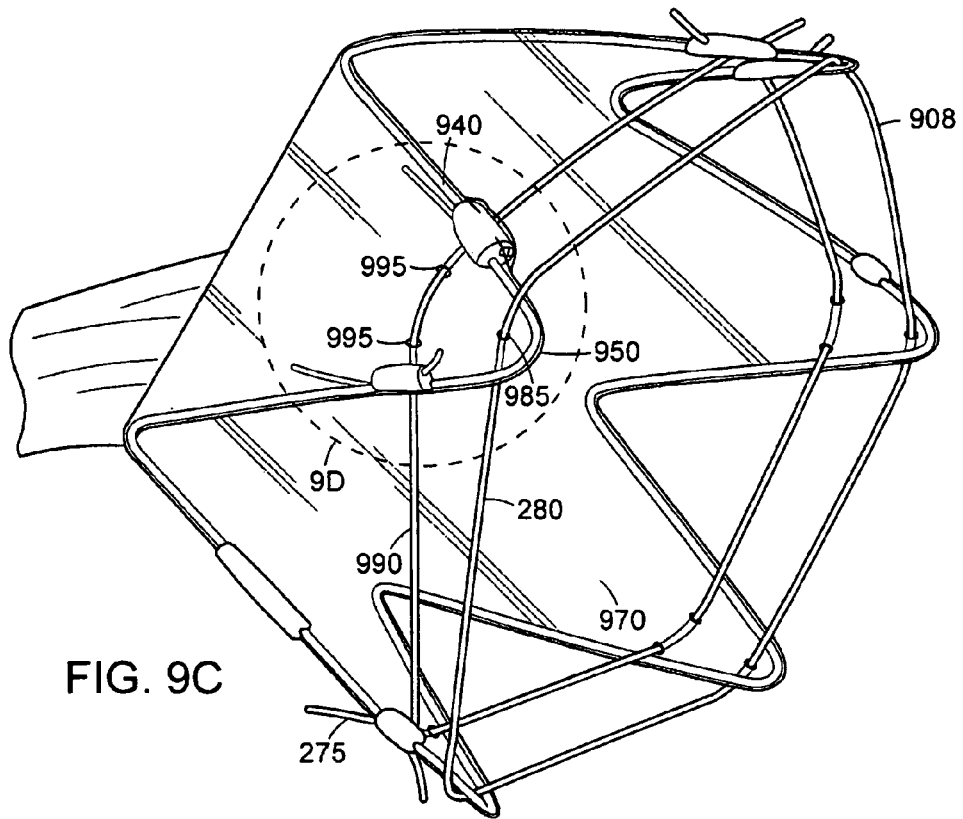
Figure 9D:
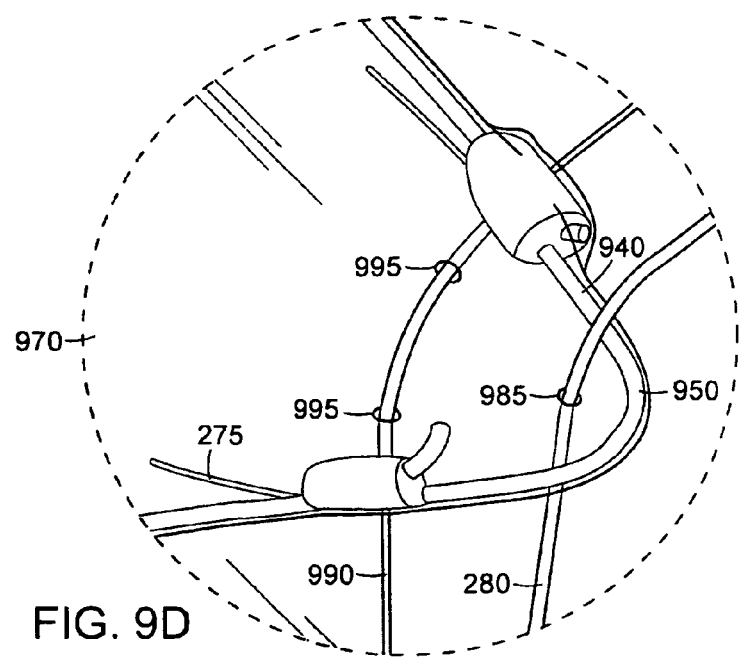

FIGS. 9C and 9D shows an embodiment of threading the proximal drawstring 280 as is illustrated in FIG. 9B. The second drawstring 990 is however, threaded through a pair of holes 995. The advantage of the approach of FIGS. 9A-9C is demonstrated by comparison of FIGS. 10A and 10B with FIGS. 11A and 11B.

Figure 10A:
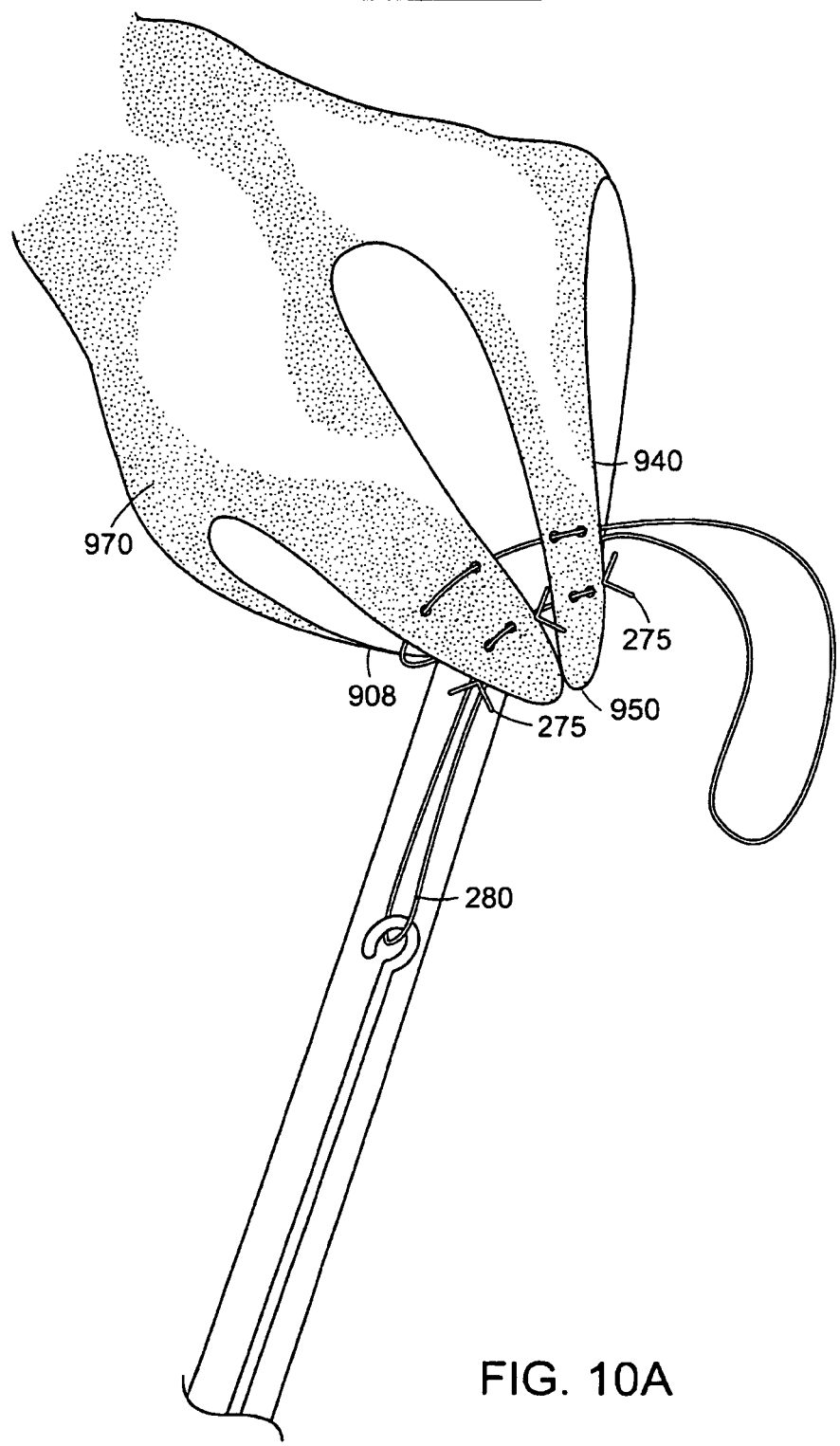
FIGS. 10A-10B show an embodiment of the gastrointestinal device with the drawstrings of FIG. 9A.
Figure 10B:
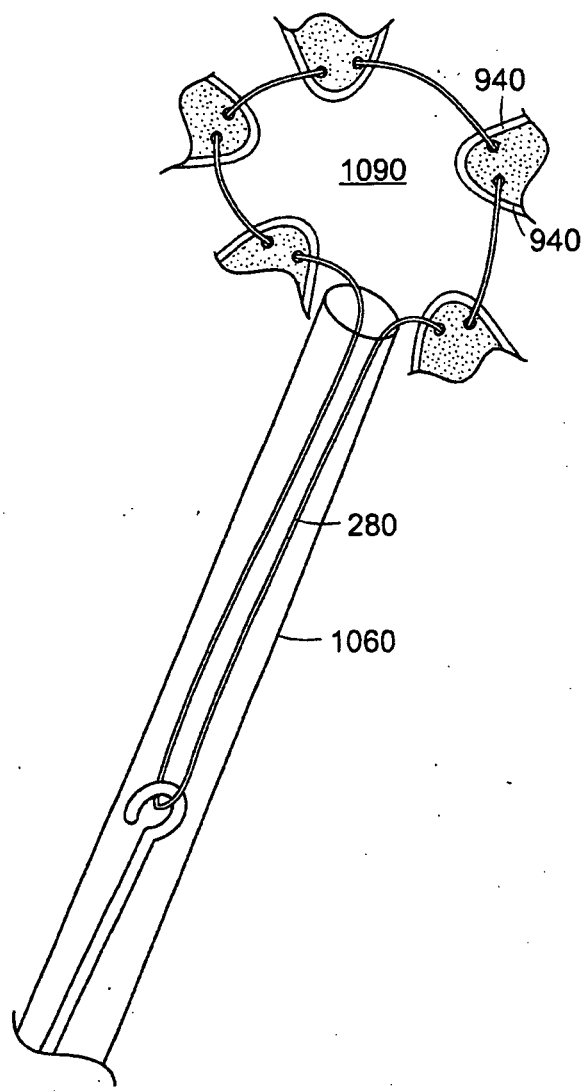

FIGS. 10A and 10B illustrate the approach of FIG. 9A. In operation, the drawstring 280 can be pulled by the retrieval device 1060 (such as the one shown in FIG. 1) as shown in FIG. 10A. The drawstring 280, when pulled, contracts about the perimeter of the anchor 908, thereby reducing the diameter of the anchor 908. Thus, the drawstring 280 can be used to facilitate removal of an implanted anchor 908 by pulling it away from the surrounding anatomy thereby extracting any barbs 275 from the surrounding muscular tissue.

Because the anchor 908 is positioned distal to the pylorus within the duodenal bulb as shown in FIG. 3A, the anchor 908 is at an angle with respect to the pylorus. When the retrieval device 1060 pulls on the drawstring 280, the webbing material 970 is pulled inward between the struts since the eyelets 980 are distal to the struts 940 on the webbing material 970. As the drawstring 280 is drawn, the tip of the retrieval device 1060, already angled relative to the anchor 908, can be caught between a pair of struts 940 rather than between all of the wave peaks 950. In that case, the retrieval device may become cocked between two struts 940 within the collapsed anchor 908. As a result, the collapsed anchor 908 has limited degrees of freedom relative to the retrieval device 1060 and can not pivot and straighten with respect to the pylorus and is thus removed at an angle with respect to the pylorus. If the drawstring 280 is not released and reengaged it becomes difficult to pull the barbs 275 into the hood 190 (as shown in FIGS. 2A-2F.) This can result in damage to surrounding tissue since the collapsed anchor 908 with barbs 275 is dragged through the intestine and pylorus sideways. Further, the esophagus is an extremely delicate area and dragging the anchor sideways with its protruding barbs could result in injury to the patient.

Additionally, pulling hard on the webbing material 970 by the retrieval device 1060 in an attempt to fully pull it into the hood 190 could cause tearing of the webbing material 970. Further, pulling on the webbing material 970 with the retrieval device 1060 to one side does not fully and uniformly collapse the anchor 908 as can be seen in the end on view of the anchor in FIG. 10B. A gap 1090, often results from this pull adding to the difficulty of pulling all of the barbs 275 into the hood 190.

Figure 11A:
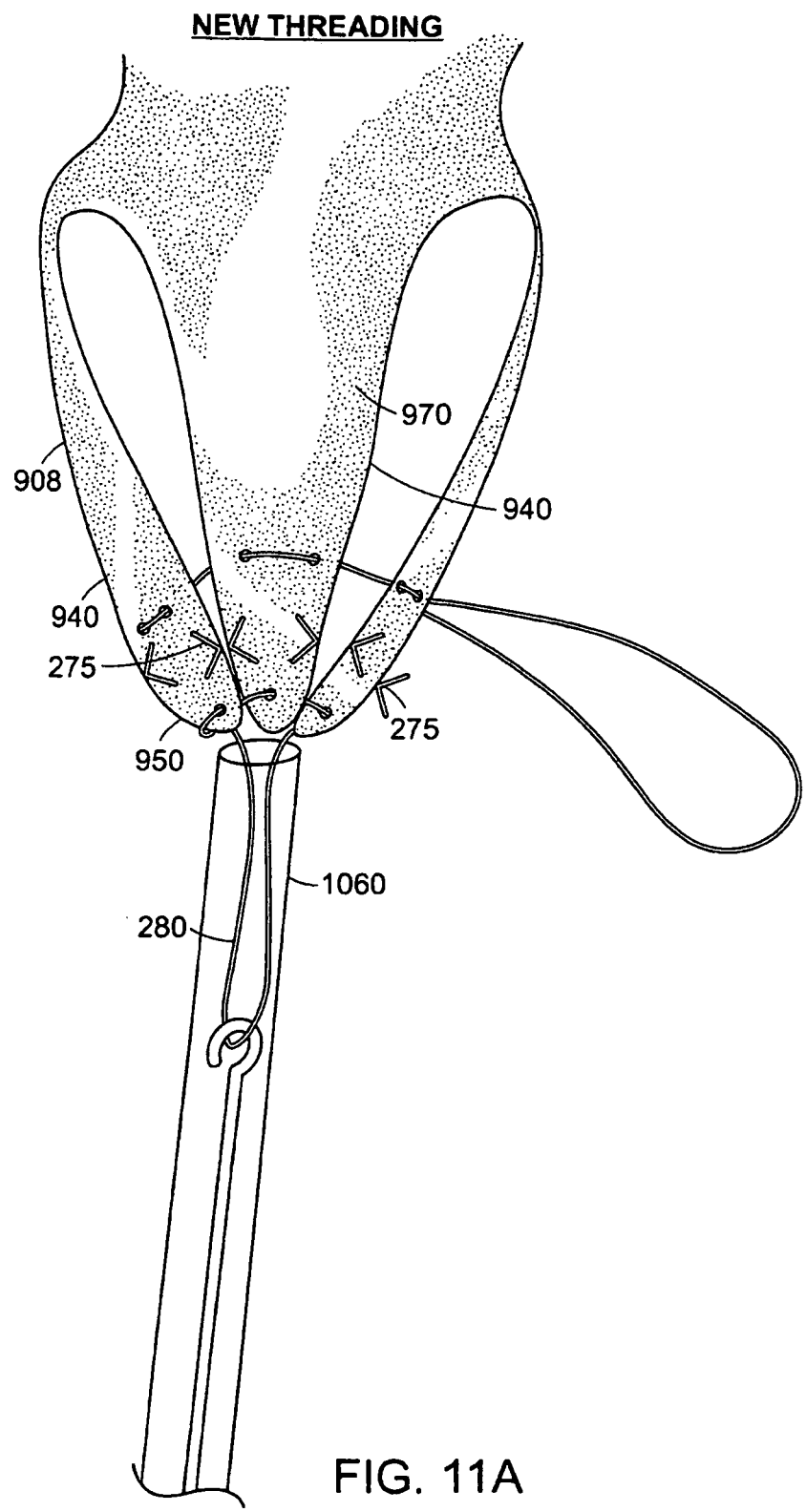
FIGS. 11A-11B show an alternate embodiment of the gastrointestinal implant device with the drawstrings of FIG. 9B.
Figure 11B:
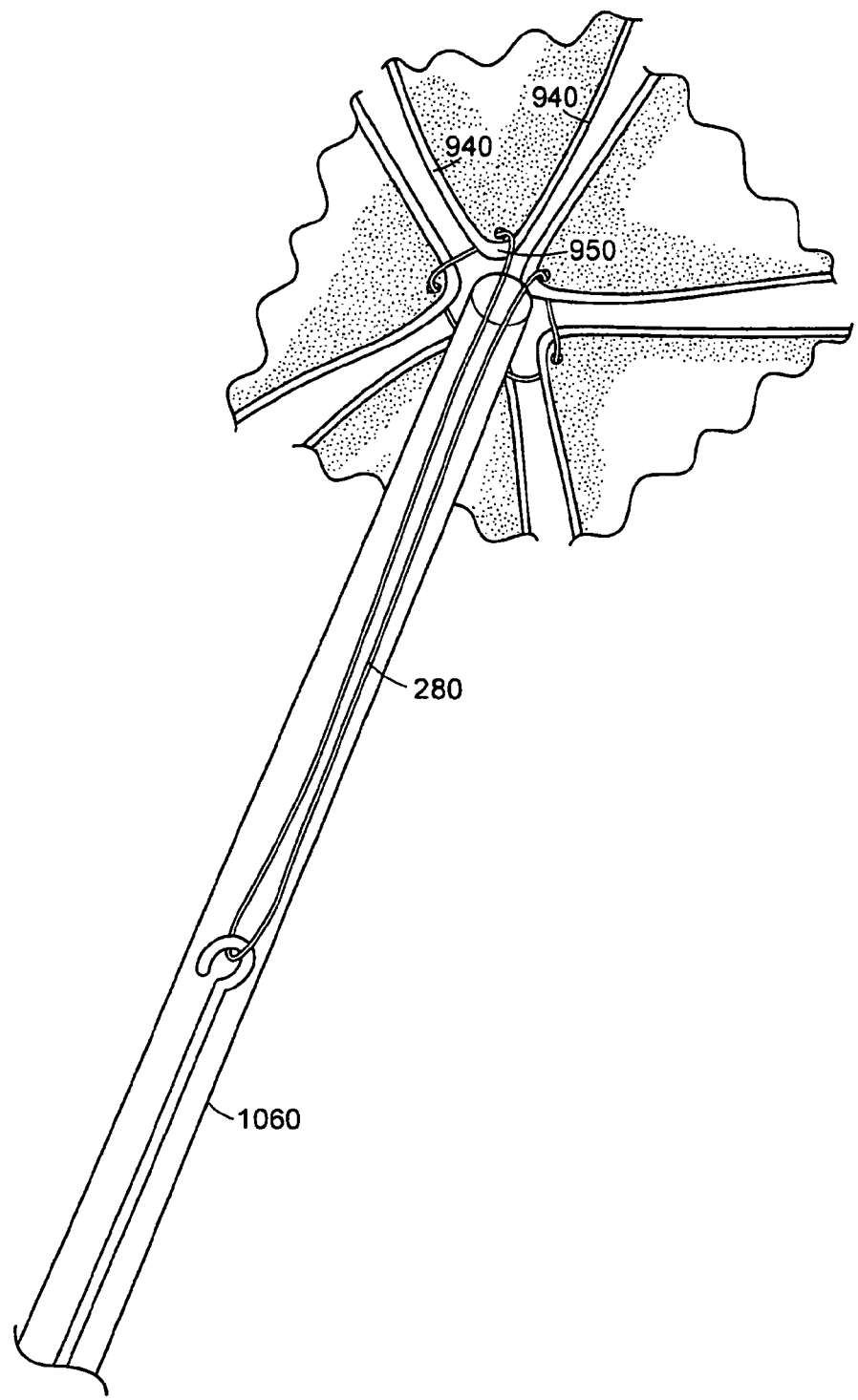

FIGS. 11A-11B shows an embodiment of threading the proximal drawstring 280 as was illustrated in FIGS. 9B-9D. The weaving of the drawstring 280 through the single hole 985 and over and under the alternate struts 940 on the proximal end of the anchor 908 near the wave peaks 950 allows the struts 940 to be pulled as opposed to the webbing material 1070, as was the case in FIG. 10A. Also, the single hole 985 can be made immediately adjacent to the wave peaks 950. In operation, when the retrieval device 1060 pulls on the proximal drawstring 280 in order to collapse the anchor, it remains proximal to wave peaks 950 of the anchor 908 on the outside of the anchor 908, as shown in the end-on view of the anchor in FIG. 11B.

This in turn allows increased degrees of freedom for the collapsed anchor 908 relative to the retrieval device 1060, since the retrieval device 1060 is not cocked between two struts 940. The anchor 908 can therefore, pivot and straighten itself with respect to the hood 190 in the pylorus as it is pulled into the hood.

Further, because the wave peaks 950 are pulled, as opposed to the webbing material 970, there results a more complete and uniform collapse as shown in FIG. 11D. The fuller collapse as well as the straightening of the anchor 908 allows for the anchor 908 and barbs 275 to be easily captured by a capturing mechanism, such as the flared hood 190. This reduces the risk of damage to surrounding tissue since the collapsed anchor 908 can be dragged out of the body straight through the gastrointestinal tract with at least the proximally directed barbs 275 fully enclosed in the hood 190.

Additionally, the pulling of the wave peaks 950 as opposed to webbing material 970, makes the tearing the webbing material 970 less likely and inconsequential. The greater strength of the suture material forming the drawstrings 280 and 990 now becomes the weakest link in the retrieval system.

While this invention has been particularly shown and described with references to preferred embodiments thereof, it will be understood by those skilled in the art that various changes in form and detail may be made therein without departing from the scope of the invention encompassed by the appended claims.

What is claimed is:

1. A device combining a positioning device for positioning an implantable device within a natural bodily lumen with the implantable device, comprising:
    an endoscope defining a lumen, the endoscope providing an outer tube of the positioning device;
    an inner tube defining a lumen and adapted for insertion into the endoscope;
    an elongated member having a proximal end and a distal end, the elongated member slidably disposed within the lumen of the inner tube;
    a grasper disposed at the distal end of the elongated member, adapted to engage the implantable device to collapse at least a portion of the implantable device when operated;
    an atraumatic flared retrieval hood attached to and fitting over the distal end of the endoscope; and
    the implantable device, wherein the implantable device comprises:
        a flexible, floppy sleeve, open at both ends, to extend into the duodenum;
        a collapsible anchor coupled to a proximal portion of the sleeve; and
        a drawstring threaded through a proximal end of the anchor and drawn into the inner tube by the grasper;
    at least a proximal portion of the anchor being captured within the retrieval hood.

2. The device of claim 1, wherein the elongated member is a wire.

3. The device of claim 1, wherein the grasper is a hook.

4. The device of claim 1, wherein the grasper is a spade.

5. The device of claim 1, wherein the grasper is a rat-tooth grasper.

6. The device of claim 1, wherein the inner tube is flexible.

7. The device of claim 1, wherein the retrieval hood is flexible transparent plastic.

8. The device of claim 1, wherein the retrieval hood includes an alignment feature to facilitate engagement of the implantable device.

9. The device of claim 8, wherein the alignment feature of the retrieval hood is an interior ramp.

10. The device of claim 1, wherein the elongated member is rotatably disposed within the lumen of the inner tube.

11. The device of claim 1, further comprising a retrieval locking mechanism for locking the grasper with respect to the retrieval hood.

12. The device of claim 1, further comprising a radiopaque marker marking the distal end of the inner tube.

13. The device of claim 1, further comprising a grasper locking mechanism to lock the grasper in place relative to the inner tube once the implantable device is collapsed.

14. The device of claim 1, wherein the implantable device further comprises at least one barb extending from the exterior surface of the anchor.

15. The device of claim 1, wherein the implantable device further comprises at least one protrusion extending from the exterior surface of the anchor.

* * * * *